United States Patent
Brumfield

(10) Patent No.: US 10,898,141 B2
(45) Date of Patent: Jan. 26, 2021

(54) SYSTEM AND METHOD FOR CHARACTERIZING RESPIRATORY STRESS

(71) Applicant: Intelomed, Inc., Wexford, PA (US)

(72) Inventor: Anne Brumfield, Cranberry Township, PA (US)

(73) Assignee: Intelomed, Inc., Wexford, PA (US)

( * ) Notice: Subject to any disclaimer, the term of this patent is extended or adjusted under 35 U.S.C. 154(b) by 758 days.

(21) Appl. No.: 15/267,919

(22) Filed: Sep. 16, 2016

(65) Prior Publication Data

US 2018/0078212 A1 Mar. 22, 2018

(51) Int. Cl.
*A61B 5/00* (2006.01)
*A61B 5/024* (2006.01)
*A61B 5/08* (2006.01)

(52) U.S. Cl.
CPC ........ *A61B 5/7246* (2013.01); *A61B 5/02416* (2013.01); *A61B 5/0816* (2013.01); *A61B 5/7257* (2013.01); *A61B 5/7278* (2013.01); *A61B 5/742* (2013.01); *A61B 5/746* (2013.01)

(58) Field of Classification Search
None
See application file for complete search history.

(56) References Cited

U.S. PATENT DOCUMENTS

| | | | | |
|---|---|---|---|---|
| 6,126,595 A | * | 10/2000 | Amano | A61B 5/02 600/300 |
| 6,129,675 A | * | 10/2000 | Jay | A61B 5/0205 600/323 |
| 2002/0058876 A1 | * | 5/2002 | Chen | A61B 5/021 600/485 |
| 2003/0163050 A1 | * | 8/2003 | Dekker | A61B 5/0205 600/483 |
| 2003/0199770 A1 | * | 10/2003 | Chen | A61B 5/021 600/485 |

(Continued)

OTHER PUBLICATIONS

Twelve-page International Search Report for PCT/US17/5206 dated Sep. 18, 2017.

(Continued)

*Primary Examiner* — Michael R Bloch
(74) *Attorney, Agent, or Firm* — Wood Herron & Evans LLP

(57) ABSTRACT

A system and method for evaluating the respiratory health of a patient and indicating and characterizing respiratory stress includes a sensor in operative communication with a patient for generating at least one biological signal, having a waveform curve in the time domain. The biological signal is processed and a waveform curve is computed, reflective of the respiration rate of the patient. A correlation is then determined between the biological signal waveform curve and respiration rate waveform curve and a respective correlation coefficient is determined. Frequency analysis is performed on the biological signal and a determination is made of a respiration metric reflective of the ratio of spectral components associated with the respiration component of the biological signal in relation to the total spectral components for the biological signal. The correlation coefficient and the respiration metric are combined to form a respiratory stress metric for displaying to a user.

19 Claims, 27 Drawing Sheets

(56) References Cited

U.S. PATENT DOCUMENTS

| | | | |
|---|---|---|---|
| 2004/0260186 A1* | 12/2004 | Dekker | A61B 5/0205 600/483 |
| 2005/0070774 A1* | 3/2005 | Addison | A61B 5/14551 600/323 |
| 2005/0148893 A1* | 7/2005 | Misczynski | A61B 5/04005 600/513 |
| 2006/0217615 A1* | 9/2006 | Huiku | A61B 5/08 600/484 |
| 2007/0213619 A1* | 9/2007 | Linder | A61B 5/02416 600/481 |
| 2013/0036718 A1 | 2/2013 | Nelson et al. | |
| 2013/0262730 A1* | 10/2013 | Al-Ali | G16H 10/60 710/303 |
| 2014/0275887 A1 | 9/2014 | Batchelder et al. | |
| 2014/0276175 A1 | 9/2014 | Banet et al. | |
| 2014/0364750 A1 | 12/2014 | Brumfield et al. | |
| 2015/0150515 A1 | 6/2015 | Strachan | |
| 2015/0190088 A1 | 7/2015 | Chen et al. | |
| 2016/0045154 A1 | 2/2016 | Addison et al. | |

OTHER PUBLICATIONS

European Patent Office; Extended Search Report in related European Patent Application No. 17851715.7 dated May 4, 2020; 7 pages.

\* cited by examiner

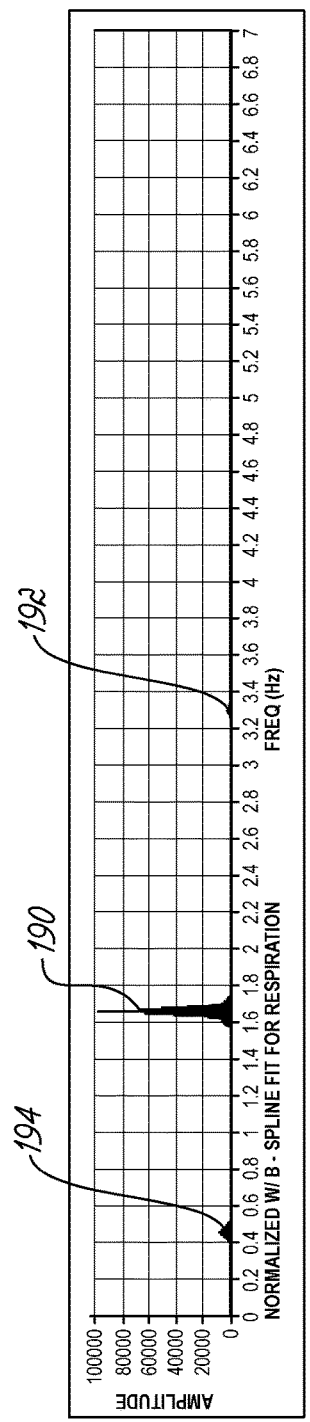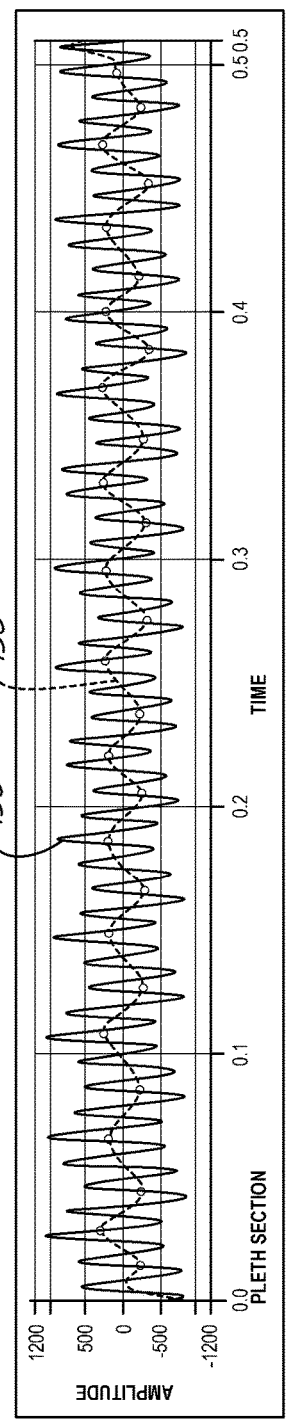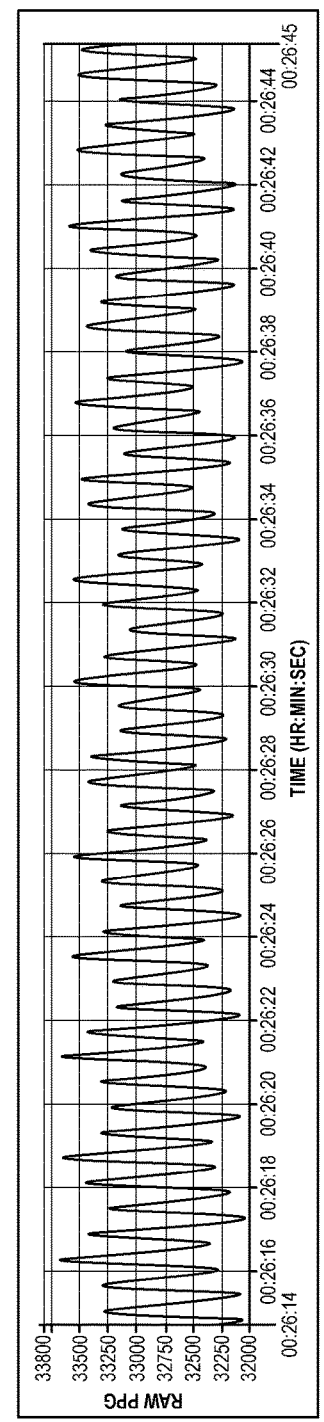
FIG. 13A
FIG. 13B
FIG. 13C

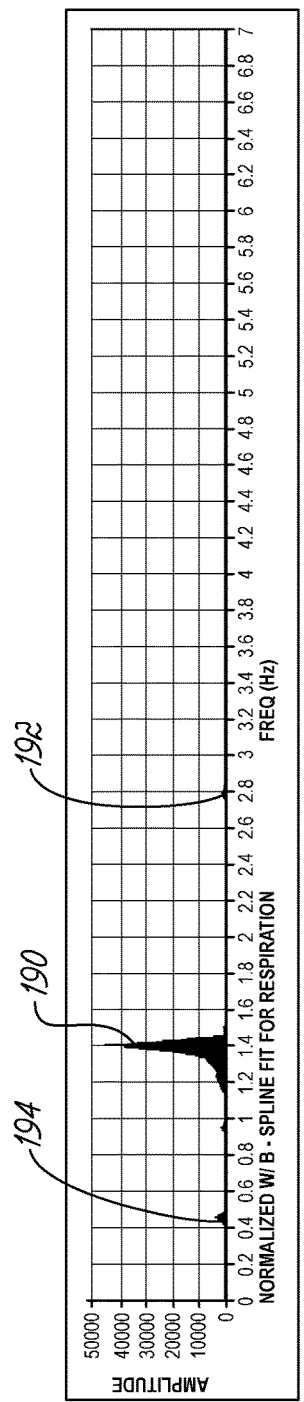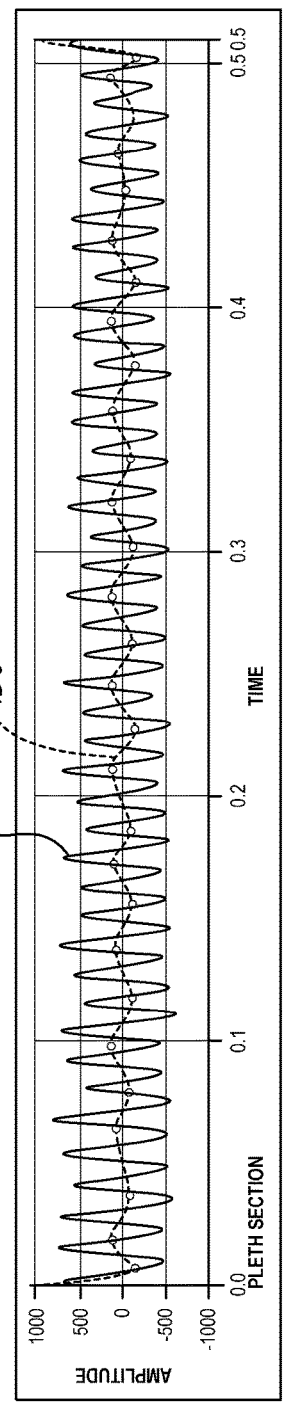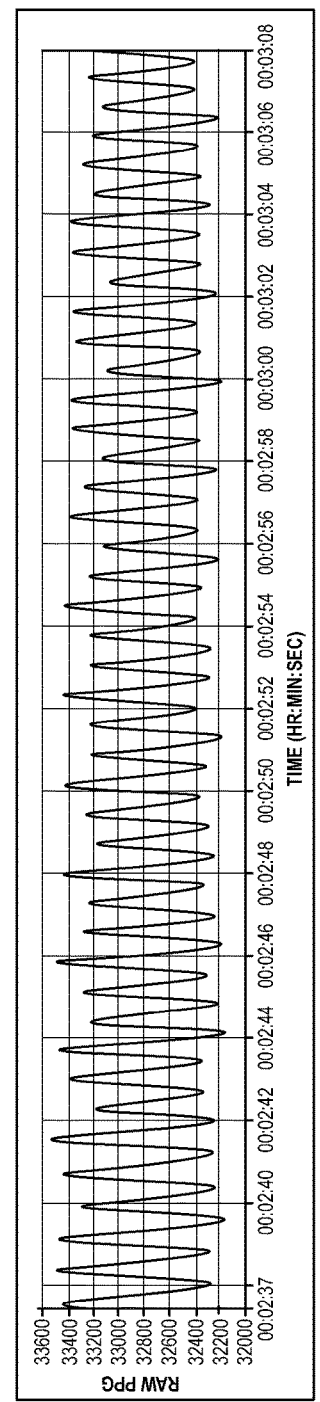

SYSTEM AND METHOD FOR CHARACTERIZING RESPIRATORY STRESS

FIELD OF THE INVENTION

The invention is directed generally to the monitoring of respiratory conditions of a person, and more particularly to categorizing when a person is at a level of respiratory stress that requires an intervention by a caregiver.

BACKGROUND OF THE INVENTION

The circulatory flow of blood for delivering oxygen and nutrients to tissues and organs and for removing toxins and wastes therefrom is an important factor in the health of a human being. Such a delivery and removal process is essential to maintaining cellular function and tissue and overall organ health. The circulatory blood flow depends upon the conditions of both the lungs and the heart of an individual, such that a stress or failure in one system detrimentally affects the other.

In the circulatory system, adequate blood flow must be maintained under varying forms and degrees of stress, which stress can be the aggregate impact of various physical, pathological, and environmental factors to which a person is exposed. In order to remain in what is considered a physiologically homeostatic state, the body must continuously adjust the various systems in order to meet constantly-changing demands. In a healthy patient, such adjustment will generally occur without a significant impact on the person. However, in situations where a person's ability to adjust is inadequate during a time of stress, the delivery of oxygen and nutrients to tissues and organs and the removal of toxins and wastes therefrom may be inadequate to meet cellular demands. As a result, overall physiological function is compromised.

Such compromise may be the result of the failing health of a person, or may be associated with one or more stressful procedures or interventions the person is undergoing, often as a result of failing health, or some medical condition or ailment. As a result, respiratory stress may develop that significantly impacts the delivery of oxygenated blood to the tissues. Some stress is the result of conditions such as Chronic Obstructive Pulmonary Disease (COPD), pulmonary edema, or apnea. In other situations, respiratory stress may be brought on by a procedure that is undertaken for one or more medical reasons.

One illustrative example of a medical intervention that may cause respiratory stress is a hemodialysis procedure. Generally, a person that has failing kidneys will undergo regular dialysis procedures for supplementing kidney function, such as the removal of waste products, elimination of extra bodily fluid, and restoring electrolyte balance. Such procedures are very stressful on the body, and require that an already compromised circulatory system be able to respond to significant stress. As a result, such a procedure may create significant respiratory stress that is often only recognized by a caregiver when the patient actually says they are feeling short of breath or gives some other indication of the respiratory stress.

While there are various systems and methods that may be good predictors of overall cardiovascular and respiratory conditions resulting from long-term pathological and age-related changes, such systems generally cannot characterize the functional adequacy of a circulatory or respiratory system in the short term. As such, in the face of significant stress on the circulatory and respiratory systems, the resultant deficiencies in supplying the demands of the tissue and organs is often not detected until a physiological function is so compromised that tissue and organ dysfunction become symptomatic and the sustainability of the person becomes at risk. In the noted example of an ongoing stressful procedure, such as a dialysis procedure, the procedure may have to be stopped indefinitely, thus preventing a patient from receiving the full benefits of such a procedure.

Accordingly, there is a need for systems and methods that are able to determine the conditions of respiratory stress and recognize various respiratory conditions that are harmful to a patient, so that the proper intervention can be determined. There is a need for such systems and devices that readily provide short-term feedback to a clinician or caregiver so that they may characterize the adequacy of respiratory and circulatory systems over short-term time intervals. In that way, any deficiencies may be readily detected and treated before the patient's sustainability is at risk. The present invention addresses these and other needs in the art, as discussed herein.

SUMMARY OF THE INVENTION

A system and method for evaluating the respiratory health of a patient and indicating and characterizing respiratory stress includes a sensor in operative communication with a patient for generating at least one biological signal, having a waveform curve in the time domain. The biological signal is processed and a waveform curve is computed that is reflective of the respiration rate of the patient. A correlation is then determined between the biological signal waveform curve and respiration rate waveform curve and a respective correlation coefficient is determined. Frequency analysis is performed on the biological signal and a determination is made of a respiration metric reflective of the ratio of spectral components associated with the respiration component of the biological signal in relation to the total spectral components for the biological signal. The correlation coefficient and the respiration metric are combined to form a respiratory stress metric for displaying to a user. Further processing involves calculating a respiration rate and evaluating the respiration rate and the respiratory stress metric to determine a respiratory stress condition for displaying to a user.

BRIEF DESCRIPTION OF THE DRAWINGS

FIG. 7A is a graphical representation of a Respiratory Stress Index in accordance with the invention, while FIG. 7B is a table reflective of the graphical representation.

FIGS. 13A-13C are graphical representations of frequency-domain and time-domain signals reflective of biological signals of a person similar to the time-domain and frequency-domain FIGS. 9A-9C that are analyzed in accordance with the present invention and reflect another respiratory stress condition and FIGS. 14A-14C are similar representations as in FIGS. 10A-10C for another different person.

DETAILED DESCRIPTION OF THE INVENTION

Figure 1:
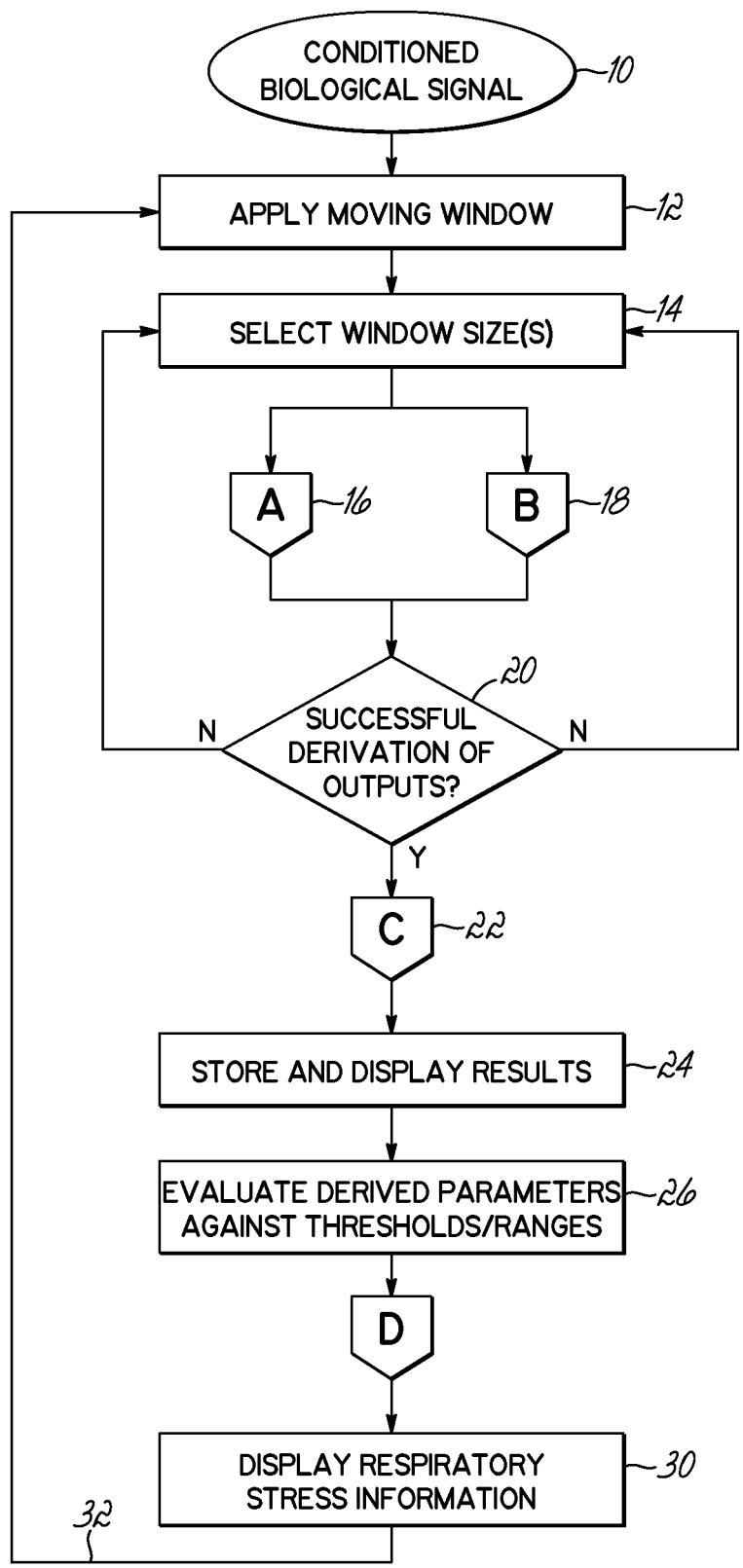
FIG. 1 is a flowchart of signal processing flow in accordance with one embodiment of the invention.

The present invention provides a way of characterizing respiratory stress that may develop in a monitored person. Such respiratory stress may be due to failure in the overall respiratory and/or circulatory systems, or due to a stressful procedure or situation that a person is enduring, where their body cannot adequately compensate. The invention does so by providing a unique analysis of respiratory and cardiac portions of biological waveforms. The invention uses both a time-domain and frequency-domain analysis of the biological waveform, including frequency analysis of respiratory and cardiac components of a biological signal that is detected from a person. The processing of the invention evaluates such spectral components and their correlation to determine when the respiratory content of the biological signal overtakes a cardiac component. From such analysis, a unique index is developed providing a real-time and useable parameter reflective of the respiratory stress of a person so that a caregiver can determine an adequate intervention and the effects of such an intervention.

The present invention is directed to a system and method for characterizing respiratory stress, or rather, abnormal respiration characteristics in order to determine when a person is undergoing significant respiratory stress for the purposes of a suitable intervention. The present invention is further directed to providing a system and method for categorizing the inter-relation between respiration and cardiac cycles in order to alert a medical caregiver that a particular person may require an intervention. The invention goes beyond simply respiration rate, and determines when respiratory efforts dominate, and possibly overwhelm the cardiac signal of a patient. The invention provides a readily-usable index for display to a caregiver, and for use in the ultimate diagnosis of the respiratory stress and abnormal respiratory conditions that a person is undergoing.

The present invention also provides a unique way of analyzing and processing a biological signal to evaluate the cardiac and respiratory components of that signal, and to evaluate their inter-relation and interaction, and display alerts regarding the respiratory stress for intervention. As noted, both time-domain analysis and frequency-domain analysis are made on the biological signal for the evaluation of the respiratory stress and the display of usable, readily-available information related thereto. Specifically, various parameters are determined from a measured biological signal, and processing and combined in a unique fashion, in accordance with aspects of the invention, for providing useful information to the caregiver. The biological signal is acquired in a non-invasive manner, with few risks to a person. As discussed herein, various different sensors might be utilized for the purposes of the invention to provide the necessary biological signals for analysis.

Respiratory stress may be caused by a variety of different physical conditions, circumstances, and health conditions. As such, the present invention may be utilized to provide the detection of respiratory stress for a variety of different people. In one use of the invention, a patient having a health condition may be monitored, including those patients that may be undergoing some particular medical procedure or treatment to their body that may cause such respiratory stress. In another use of the invention, a healthy person may be monitored undergoing a physically stressful activity. Therefore, the invention is not limited to use with a healthcare patient, per se.

For example, various different procedures might be performed on a patient to address other health issues of the patient that are not specifically or directly related to the respiratory and/or cardiac systems, but which may have an overall impact on such systems. One such procedure is a hemodialysis procedure that is utilized with patients that are experiencing kidney failure. For example, as blood and other fluids are removed from a patient for the hemodialysis filtering process, a significant amount of respiratory stress may be created deep into the dialysis process. If such stress is not recognized in a timely fashion for a suitable intervention, the entire dialysis process may need to be stopped to provide a more vigorous medical intervention with the patient. The present invention, however, is not limited to dialysis processes, and thus, can be utilized for detecting respiratory stress in patients undergoing other procedures or are being treated for other clinical conditions. Also, as noted, it may be used with generally healthy patients that may experience particular conditions that create respiratory stress that then requires some particular intervention from the person themselves or by a caregiver who is monitoring the person. However, for illustrative purposes and discussion herein, a person on which the invention is used is referred to as a "patient", and person using the information is referred to as a "caregiver", although those terms are not limiting with respect to the invention.

In the past, the respiratory rate has been utilized to alert the caregiver to a slow or fast breathing cycle in a patient. However, such minimal information generally does not recognize the interplay between the respiration cycle and the cardiac cycle. All the current evaluations of abnormal respiration, as a result, are often of a somewhat qualitative nature, for example, deep breathing versus shallow breathing, or rapid breathing versus slow breathing. The present invention provides a further unique analysis, both in the frequency-domain and time-domain of a biological signal for providing additional information, rather than just respiratory rate to a caregiver or clinician. The analysis is used to provide a respiratory stress index (RSI) parameter that reflects a stress condition and that can be used to diagnose one or more respiratory conditions.

In accordance with one embodiment of the invention, the biological signal utilized is a photoplethysmogram signal, "pleth" signal or PPG signal, which is a biological signal optically obtained using a sensor similar to that used for obtaining a pulse oximetry reading. PPG signals are well known and sensors for obtaining such signals are also readily available. The obtained biological signal, such as the PPG signal, is then processed in accordance with the present invention utilizing both time-domain analysis and frequency-domain analysis of the biological signal in order to evaluate and characterize respiratory stress. Although a PPG signal is used in one embodiment of the invention, other biological signals might also be used to reflect cardiac and respiratory components for analysis, and so the invention is not limited to use of just a PPG signal. The signal is processed utilizing a computer or other suitable processing system or device, such as a processing system provided by a mobile device (e.g., a pad device). However, other computer systems and processing systems may be implemented, and thus, the invention is not limited to the specific device or system from which the invention may be implemented. One suitable device for implementing the invention is the CVInsight® Patient Monitoring & Informatics System available from Intelomed, Inc. of Wexford, Pa. The CVInsight® System is implemented on a tablet device having a suitable touch screen and display for the purposes of displaying the outputs of the invention and the specific respiratory stress index and diagnosis, as discussed herein.

Turning to FIG. 1, a flowchart is illustrated for the purposes of explaining one embodiment of the invention. Such program flow and program flow paths will be executed in suitable software in a processing device or system, as discussed herein. While the program flow is illustrated in the particular arrangement for explanation and discussion of the invention, the invention is not limited to a specific order for each of the steps or a specific hardware and software environment, and thus, some deviation may be utilized in the processing of the biological signal, as disclosed herein.

Turning to FIG. 1, the conditioned PPG signal is obtained from a suitable sensor. Various usable sensors for obtaining biological signals that may be useful for the invention, such as a PPG signal, are set forth in Table 2 below as discussed. The sensor may be non-invasively attached to the patient, such as on the forehead or other location of a patient, to obtain the necessary biological signal as illustrated in block 10. The measured biological signal is conditioned and filtered is as appropriate for further signal processing. Also for processing purposes, a moving processing window is applied in the signal acquired, as shown in block 12. In one embodiment of the invention, a thirty-second moving window may be a suitable size to apply to the streaming waveform data of the biological signal, but the window size is variable. For certain breathing patterns or conditions, such as Cheyne-Stokes breathing, a larger window, such as a three-minute window, might be more appropriate to apply to the streaming waveform. The signal may be processed in accordance with the invention and the processing outputs evaluated to determine if a different sized window is desirable. As set forth in block 14, an appropriate window size or a battery of varying window sizes is selected for processing purposes.

In accordance with one aspect of the invention, time-domain analysis and appropriate numerical analysis is performed on the biological signal in combination with frequency-domain analysis. In FIG. 1, two paths—one labeled path "A", and one labeled path "B", are illustrated for the time-domain processing and frequency-domain processing in accordance with the invention. Such processing may be in parallel as shown or serially in the processing flow. After the initial analysis, the outputs may be tested or evaluated per block 20. If the derivation was not successful in one of the paths A, B, another window size may be selected, as shown in the return paths from block 20.

Figure 2:
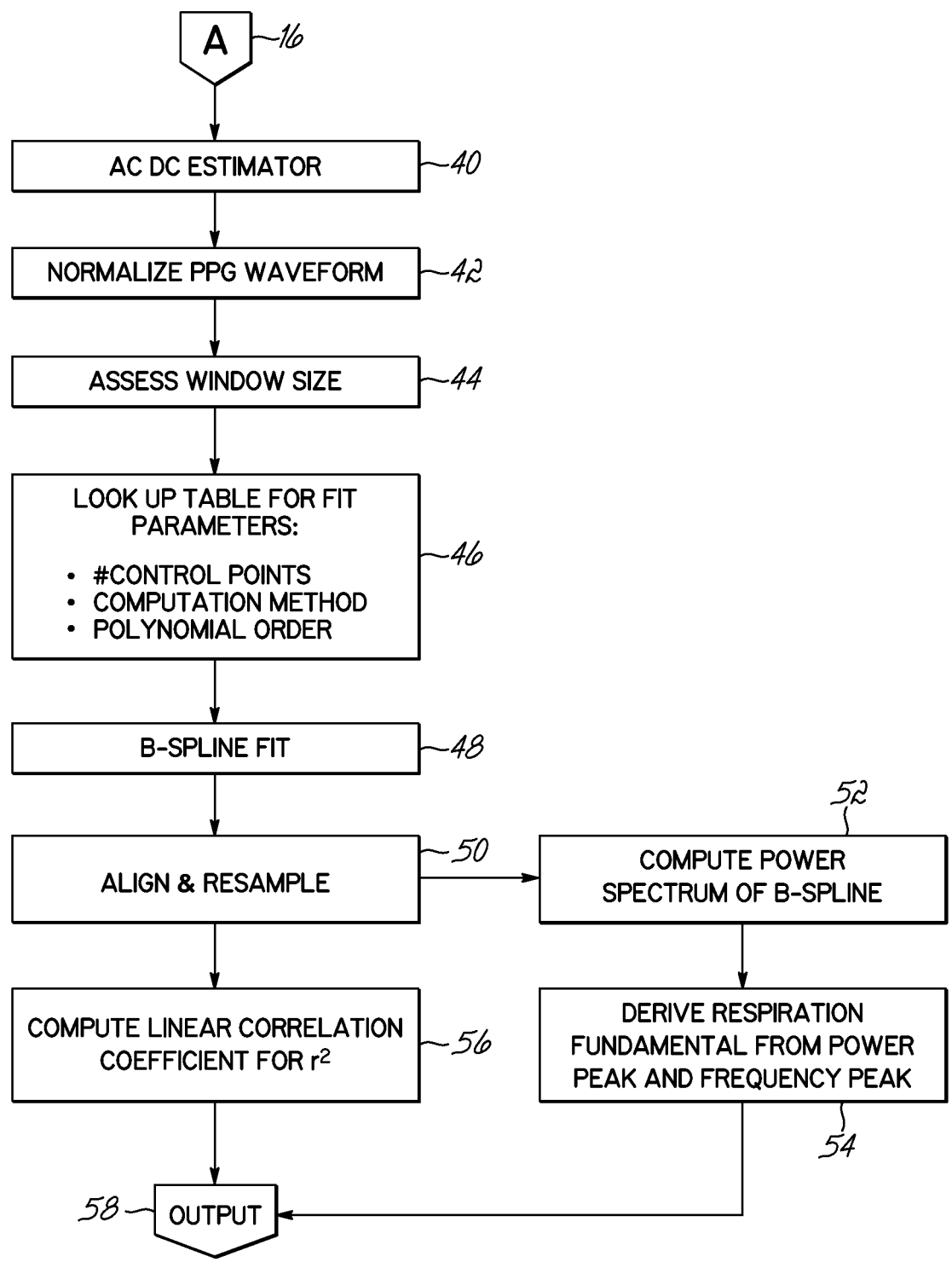
FIG. 2 is a flowchart of further signal processing flow in accordance with one embodiment of the invention.

Turning now to FIG. 2, additional program flow is illustrated for flow path A. Referring to block 40, the detected biological signal goes through an AC/DC estimator step, wherein the AC and DC components of the biological signal, such as the components of the PPG waveform, are separated. Then, the DC component may be subtracted from the PPG waveform to normalize the waveform (block 42). Next, the selected window size is assessed (block 44) to determine what type of moving window 14 was utilized for signal acquisition, as shown in FIG. 1. The selected window size will then be used to determine the appropriate time-domain analysis and linear regression analysis to be made for the points of data associated with the biological signal.

For example, the number of control points for the regression analysis, the computational method used, as well as the polynomial order of the curve fit, will be based upon the selected window size or window length. As such, in one embodiment of the invention, a suitable lookup table might be indexed by the window size for determining the parameters for the curvature fit. In one embodiment, the number of mobile control points might be, for example, 20-40 points out of a larger number of data points of the biological signal wave. This would be done for the purposes of isolating the respiration component or respiration features from the overall biological signal waveform. Furthermore, the computation method utilized for a curve fit that is used, such as a B-spline curve fit, might be selected using the window size. In one embodiment of the invention centripedal computational methods are used. However, other computation methods could be utilized, as would be understood by a person of ordinary skill in the art with respect to the regression analysis. Furthermore, as set forth in block 46, the polynomial order for the curve fit might also be selected based upon the assessed window size. In one embodiment of the invention, the polynomial order of three is utilized. However, other polynomial orders might be utilized, as would be understood by a person of ordinary skill in the art.

Next, numerical analysis is performed on the data points to yield a curve that is reflective of the respiration rate of a person from which a biological signal is obtained. That is, a particular curvature fit is done on the waveform data in order to yield a respiration rate curve. In one particular embodiment of the invention, as illustrated in FIG. 2, a B-spline fit analysis is performed for the purposes of obtaining a curve reflective of the respiration rate component within the waveform of the biological signal, such as the PPG signal (block 48).

Depending upon the window size used, as well as the number of data points of the B-spline waveform curve, that B-spline waveform would generally have less data points than the original biological signal. For example, a PPG signal may have two thousand data points, depending upon the window size. Accordingly, for the purposes of evaluating the correlation between the PPG signal and respiration curve, as discussed herein, it may be necessary to up-sample, or re-sample and align the B-spline waveform for matching the array size of the PPG signal. Generally, for the purposes of correlation, the same number of points is needed. As such, block 50 sets forth an alignment and resample step to align the B-spline fit curve for correlation processing.

Next, as shown in block 56, correlation processing is performed with respect to the PPG waveform and the B-spline waveform that is reflective of the respiration component. From that correlation processing, the linear correlation coefficient is computed, as reflected by an $r^2$ value associated with the correlation. As would be understood by a person of ordinary skill in the art, the correlation coefficient reflected by $r^2$ provides an indication of the curve fit and correlation between the PPG waveform and the B-spline curve that is reflective of the respiration component. The correlation coefficient $r^2$ is an output from process path A that is used for further processing (block 58) and for the measurement of a Respiratory Stress Index (RSI), as discussed herein.

As shown in FIG. 2, the respiration rate might also be obtained from the derived B-spline fit curve. As shown in block 52, the power provided by the spectrum analysis of the respiration related B-spline fit curve may be computed. That is, a particular power peak and frequency peak associated with the respiration fundamental frequency is obtained through appropriate frequency analysis, such as a Fast Fourier Transform (FFT) analysis of the respiration curve. Using the derived respiration fundamental frequency, the respiration rate may be obtained. That respiration rate may be returned as another output of block 58 and path A for further processing. The respiration rate devised pursuant to FIG. 2 processing steps may be compared to the respiration rate that might be derived directly from the PPG waveform, such as through similar FFT analysis. Generally, such parameters should agree, and therefore, the respiration rate derivation set forth in FIG. 2 may be a redundant, or backup, derivation for the inventive system. However, it may be necessary to use the processing steps of blocks 52, 54 when the respiration rate is such a minor portion of the PPG waveform that is difficult to detect through frequency analysis of the PPG waveform or some other biological signal waveform.

Turning again to FIG. 1, various derived outputs, as illustrated in block 58 are returned at block 16 for further processing. Referring to FIG. 1, according to block 20, a test might be made to determine whether the derivation of the outputs was successful, such as whether there was a suitably-sized window and suitable B-spline analysis and/or derivation of a respiration rate. If not, as illustrated by the return path shown in FIG. 1, a different window size might be selected. However, if the derivation of outputs through the processing signified at block 16 (FIG. 2) is suitable, the outputs are used for further processing as discussed.

In accordance with another feature of the invention, frequency analysis is also performed on the obtained biological signal, as illustrated by block 18 and process path B in FIG. 1. Block 18 and the processing flow associated with path B are reflected in FIG. 3, as illustrated. From the PPG signal, a heart rate or pulse rate may be obtained. That is, the heart/pulse rate is derived from the measured PPG signal, or other biological signal. Alternatively, the heart/pulse rate might be acquired, such as from another device, including, for example, an EKG device or a pulse oximeter device. The fundamental pulse rate frequency (Fundamental$_{PR}$) is determined simply by dividing the acquired or derived pulse rate of block 59 by sixty to yield the fundamental pulse rate frequency in hertz (Hz) (block 62). From that fundamental pulse rate frequency, the power spectrum is computed for the PPG window of the selected window size (See FIG. 1), as illustrated in block 64. That spectral frequency analysis may be performed utilizing FFT analysis, or another suitable frequency analysis algorithm for determining the power spectrum of the signal peaks reflected in the frequency spectrum of the PPG waveform. Harmonic analysis is performed for all the measurable signal frequency peaks associated with the pulse rate spectrum, including the fundamental peak, as well as the various detectable harmonic frequencies or harmonics. The amplitudes or power of the fundamental and harmonic signals are then summed to provide a sum HarmonicSum$_{PR}$ associated with the pulse rate component of the PPG signal. A similar harmonic analysis is done with respect to the frequency components of the PPG signal that are associated with respiration. Generally, for normal respiration, the respiration rate is below the pulse rate and so the fundamental frequency of the respiration rate is below the pulse rate fundamental frequency. The harmonic analysis is therefore also done with respect to the fundamental signals and associated harmonics below the Fundamental$_{PR}$ frequency signal. That is, the fundamental signal reflective of the respiration rate Fundamental$_{RR}$ is determined and the sum of the fundamental respiration rate signal and harmonics associated with the respiration rate is then determined HarmonicSum$_{RR}$, as set forth in block 70. Accordingly, the sum of the cardiac frequency components of the PPG signal is determined per block 66, while the sum of the respiratory component of the PPG signal is determined per block 70.

Figure 3:
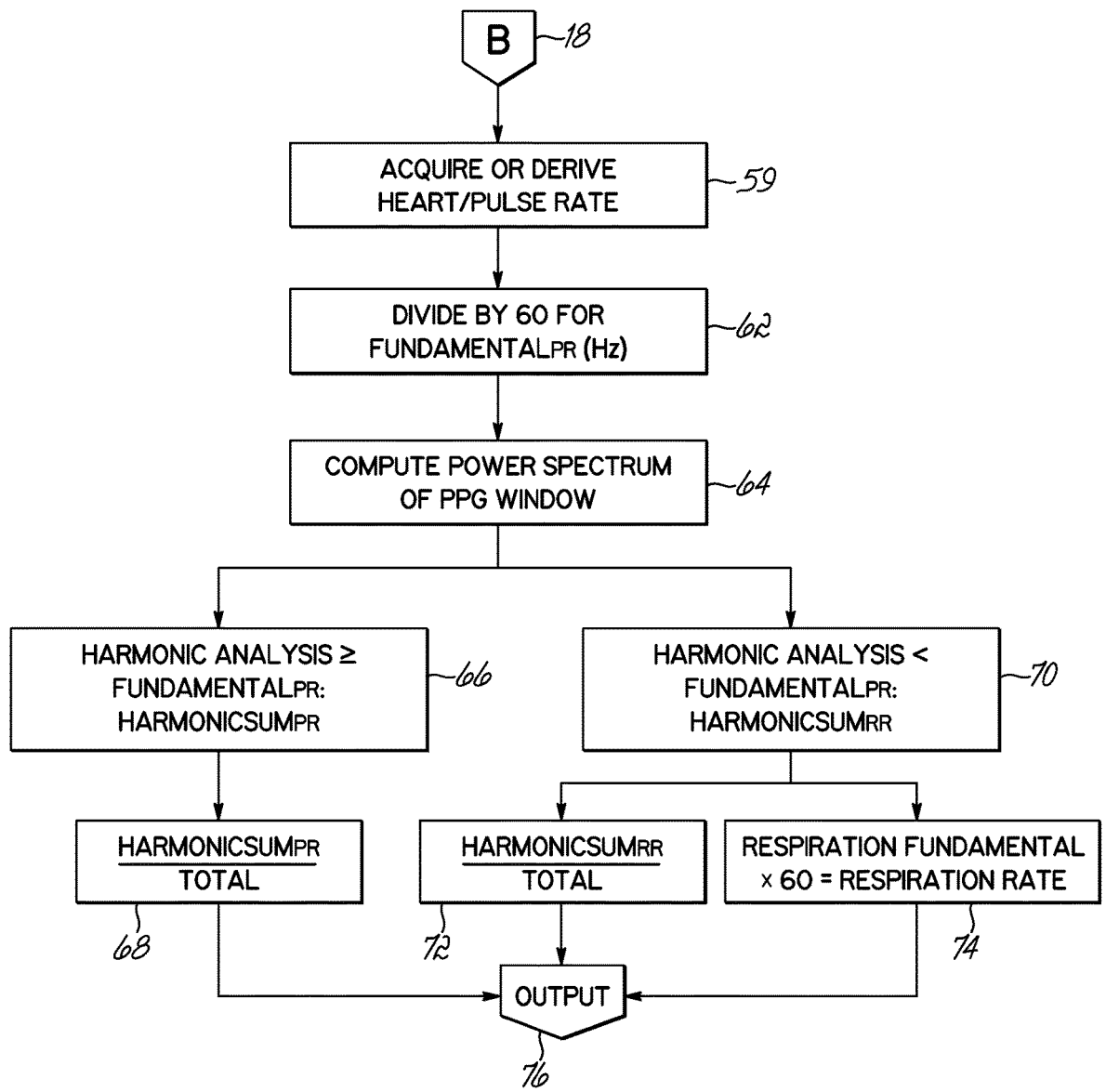
FIG. 3 is a flowchart of further signal processing flow in accordance with one embodiment of the invention.

Referring again to FIG. 3, the harmonic frequency analysis provided in the steps set forth in blocks 66 and 70 provides a sum of the power in the frequency-domain for the pulse rate fundamental frequency Fundamental$_{PR}$ and associated harmonics, and/or the power for the respiration rate fundamental frequency Fundamental$_{RR}$ and associated harmonics. The established pulse rate is used to separate the spectral components and frequency content associated with the pulse rate within the PPG waveform from the spectral content associated with the respiration rate. The sums of the spectral components of the respiration cycle and cardiac cycle are then normalized. This is done by dividing the sums of the specific spectral components of the respiration and cardiac cycles (HarmonicSum$_{PR}$, HarmonicSum$_{RR}$) by the total spectral content (Total) of both the cardiac components and the respiration components or the total of the PPG spectrum. As illustrated in FIG. 3 and the steps reflected in blocks 68 and 72, the normalized pulse rate ratio (block 68) and respiration rate ratio (block 72) are reflective of both the fundamental frequency and the harmonics for each component that are summed. It has been determined that the harmonics of the fundamental signal can have significant content, and thus, the total spectral content of each component is utilized in the normalization steps.

As may be appreciated, the ratios as determined in the steps of blocks 68 and 72 will be reflective of different portions of 100% of the total spectrum (Total). That is, some portion of the total power is from the pulse rate component, and the remaining portion is from the respiration rate component. For the purposes of establishing the respiratory stress index (RSI) as disclosed herein, the ratio associated with the respiration rate component, as set forth in block 72, may be used. Alternatively, the ratio associated with the pulse rate might be used to derive the respiration rate portion (e.g., 100−$Ratio_{PR}$). The pulse rate component ratio is referred to herein as the "Cardiorespiratory Ratio", and is a portion of the derived RSI, as discussed.

Generally, the respiration rate may also be calculated based upon the frequency analysis done on the respiration rate fundamental frequency. Generally, multiplying the respiration fundamental frequency by 60 yields the respiration rate, as set forth in block 74. The respiration rate and the normalized component of the respiration rate (block 72) are provided as outputs from process path B and FIG. 3, as illustrated at block 76. The respiration rate might also be compared to the output derived from step 54.

Returning again to FIG. 1, the output from process path B, as well as the output from process path A, are tested to determine if there was a successful derivation of those outputs, as set forth in block 20. If not, the outputs might be further derived, such as with a different window size or with the same window size as reflected in the loops from blocks 20 to block 14 shown in FIG. 1.

In accordance with one aspect of the invention, various derived outputs and parameters determined herein are utilized to provide another parameter referred to as the respiratory stress index (RSI). That RSI value, as well as the respiration rate, may then be referenced against one or more ranges and/or thresholds for determining if a patient is undergoing significant respiratory stress, and to evaluate these parameters, such as for the purposes of diagnosis of various respiratory conditions. Accordingly, the derivation of outputs made with respect to process path A, as illustrated in FIG. 2, and process path B, as illustrated in FIG. 3, would include the determination of such outputs from a patient at rest, before a procedure or other stress is placed on their cardiovascular and respiratory systems, in order to determine a baseline for comparison. As discussed further hereinbelow, in addition to displaying information associated with determined respiratory stress, a caregiver, clinician, or other person monitoring the patient may set forth the signal levels reflective of a deviation from various baselines established for the patient, such as a baseline respiratory stress index (RSI) or baseline respiration rate. As such, the baseline might be established before beginning a medical procedure, such as dialysis or some other procedure, for the purposes of such comparison.

Referring again to FIG. 1, the RSI parameters are calculated from the outputs that were successfully derived (block 20). Process C, as reflected in block 22 in FIGS. 1 and 4, utilizes the outputs derived from both the time-domain analysis and frequency-domain analysis to provide the RSI parameter, in accordance with an aspect of the invention. From the time-domain analysis and the computation of the correlation coefficient $r^2$ in the process path A, the level of correlation between the B-spline fit respiration curve and the original PPG waveform demonstrates that as the content in the PPG waveform that is contributed by the respiration component increases, such as during significant periods of respiratory stress, the $r^2$ value increases toward 1. Similarly, as respiration begins to dominate the cardiac cycle during respiratory stress, the output reflective of the respiratory ratio that is a sum of the fundamental and harmonics of the respiration rate as normalized according to process path B (FIG. 3), moves closer to 100%, reflective of the dominance of the respiratory cycle within the PPG waveform.

Figure 4:
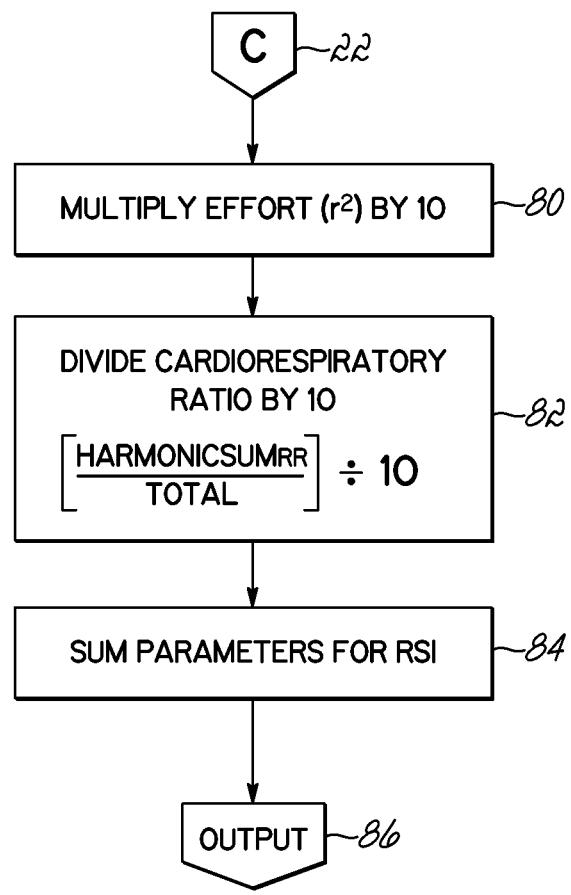
FIG. 4 is a flowchart of further signal processing flow in accordance with one embodiment of the invention.

Referring to FIG. 4, and the process path C for the derivation of RSI in accordance with the invention, in block 80, the correlation coefficient output $r^2$ is multiplied by ten. As such, the correlation component of the overall RSI progresses from 0 to 10 based upon the respiratory stress of the patient. The cardiorespiratory ratio, on the other hand, as set forth in block 82, is divided by ten, so that it progresses from 0 to 10, rather than 0 to 100, as calculated for the normalized ratio. In accordance with the invention, the parameters as derived in the process of block 80 and block 82 are then summed together to form the inventive parameter referred to as the respiratory stress index, or RSI, as set forth in block 84. That RSI value progresses from 0 to 20, and is output per block 86, for use in the overall process, as illustrated in FIG. 1.

Turning again to FIG. 1, the resultant parameters and outputs as determined by the invention may be appropriately stored in memory, and displayed, such as through a suitable graphic interface. In one embodiment of the invention, utilizing the CVINSIGHT® platform, the resultant outputs and parameters may be displayed on the touch screen. The step of block 24 is not limited, however, to the ways and means in which the various results and parameters might be displayed or stored.

Figure 5:
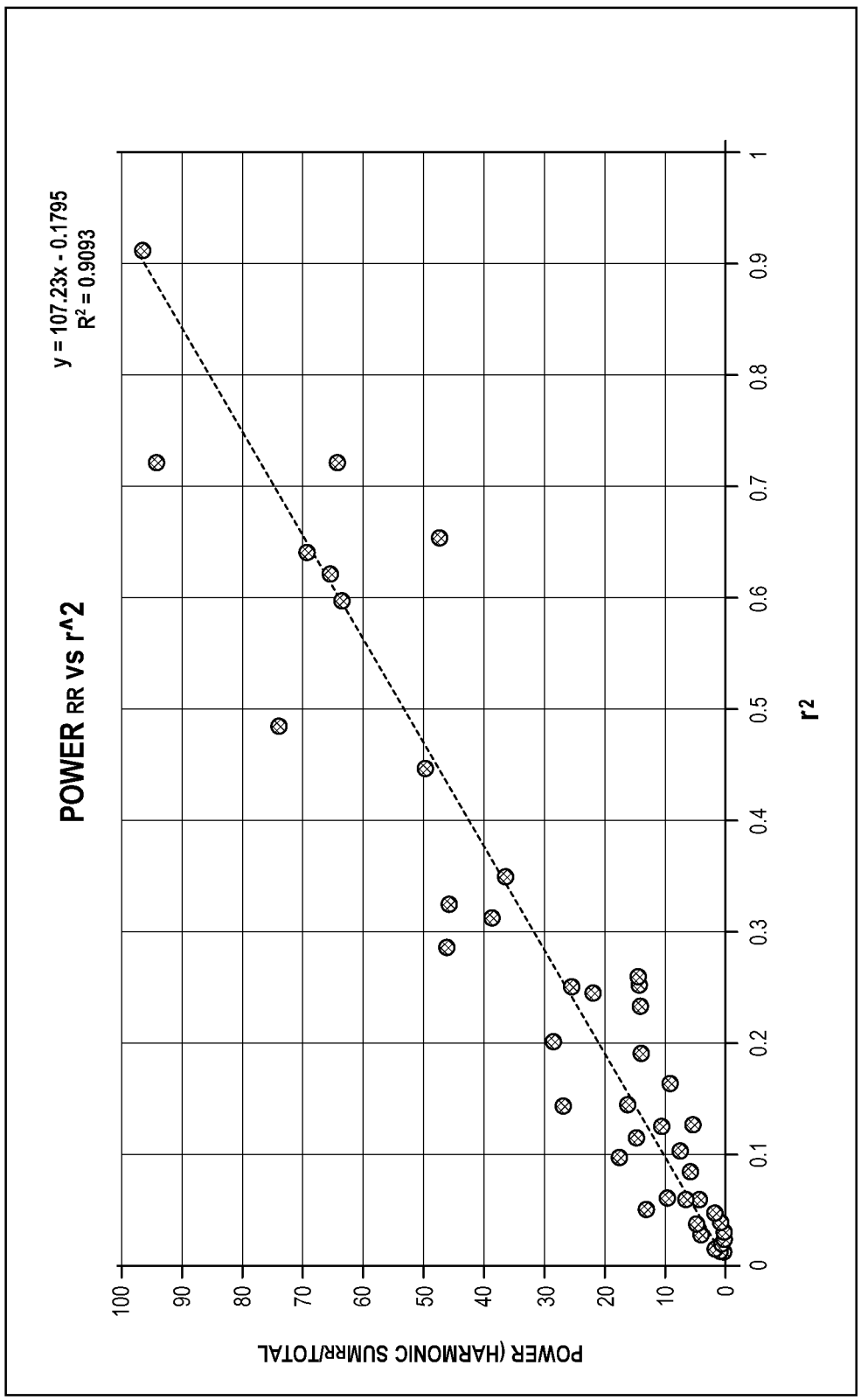
FIG. 5 is a graphical illustration of determined respiratory parameters in accordance with one aspect of the present invention.

As noted, because the $r^2$ component is adjusted to a scale of 0 to 10, and the cardiorespiratory ratio is adjusted also to a scale of 0 to 10, the RSI scale is 0 to 20. FIG. 5 illustrates a graph of the power reflected in the determined cardiorespiratory ratio (0-100) versus the determined correlation coefficient—$r^2$ (0-1), as measured for a patient in accordance with the aspects of the invention. The best linear fit resulted in an $r^2$ of 0.9093.

Figure 6:
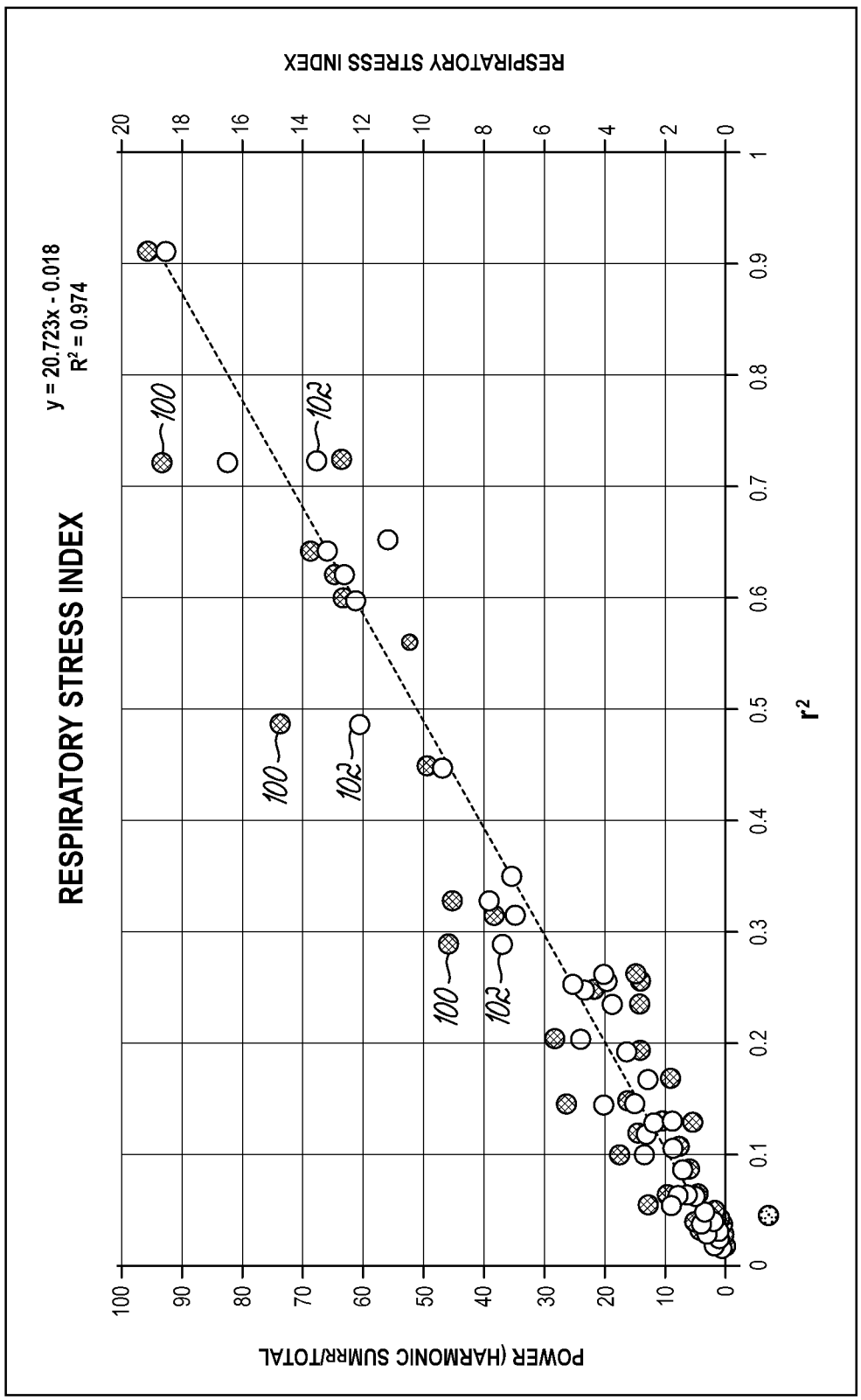
FIG. 6 is a graphical illustration of determined respiratory parameters in accordance with one aspect of the present invention.

FIG. 6 illustrates the graphical representation of the respiratory stress index versus the correlation coefficient $r^2$. Points 100 from FIG. 5 are reflected, as well as points 102 indicative of the respiratory stress index (RSI). As noted, the RSI ranges from 0-20, and is a combination of a correlation coefficient $r^2$ that is a reflection of the respiratory effort of a patient, as well as the cardiorespiratory ratio that conveys the harmonic content of respiration in the overall PPG waveform. The best linear fit resulted in an $r^2$ of 0.974.

As noted herein, when a sensor in the inventive system is first applied to a patient, measurements are made to provide a baseline with respect to the RSI parameter. Certain patients may be experiencing various ailments or conditions, which would give them a somewhat elevated RSI initially, and thus, the invention can address the preliminary conditions, as well as the worsening of respiratory conditions, and the further appearance of respiratory stress in the patient progression. In one aspect of the invention, it may be used to monitor a patient that is undergoing a medical procedure.

Figure 7:
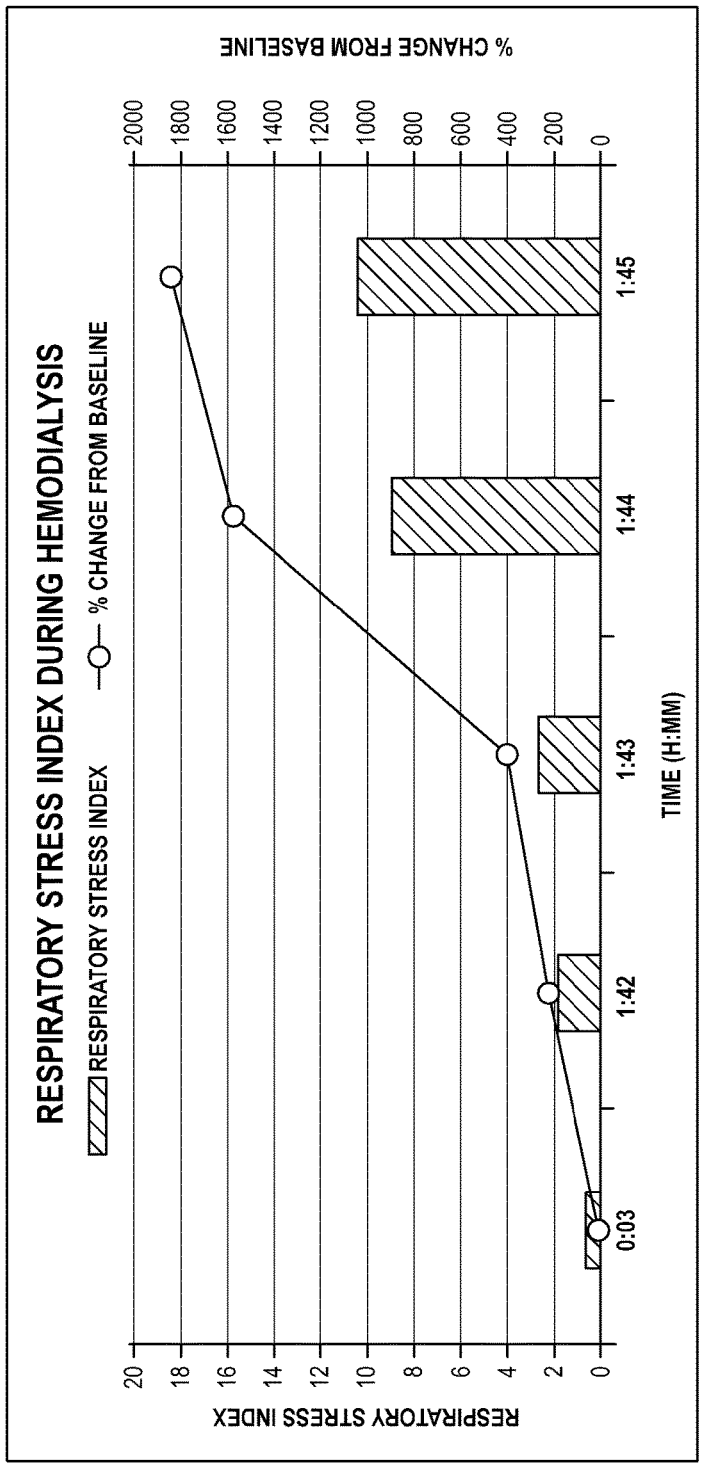

FIG. 7A is a graphical representation of a respiratory stress index that was measured during a procedure, such as hemodialysis, indicating both the measured RSI parameter, as well as the percent of change from the initial baseline.

FIG. 7B is a table of values used for the graph of FIG. 7A, showing the various components of RSI in accordance with the invention, as well as the adjusted parameters that are used to yield the respiratory stress index RSI parameter. For example, as illustrated, the correlation coefficient $r^2$ is adjusted by multiplying by ten, whereas the cardiorespiratory ratio is adjusted by dividing by ten, with the two numbers added for providing a respiratory stress index in accordance with the invention. Referring to FIG. 7A, it may be seen that the RSI is very low at the beginning of the hemodialysis process, and provides a baseline. But, at one hour and forty-two minutes into the hemodialysis process, there has been a significant increase in RSI, and a significant percentage change in baseline over each of the next minute intervals 1:43, 1:44, and 1:45, indicating significant respiratory stress that is taking place.

Referring again to FIG. 1, once the results are obtained and an RSI determined as a measurable parameter, the RSI and other parameters, such as respiration rate, may be evaluated against one or more thresholds and ranges, such as for diagnosing respiratory stress or other stress conditions. For such an evaluation, the processing flow progresses to process path D, as illustrated in FIG. 8.

Figure 22:
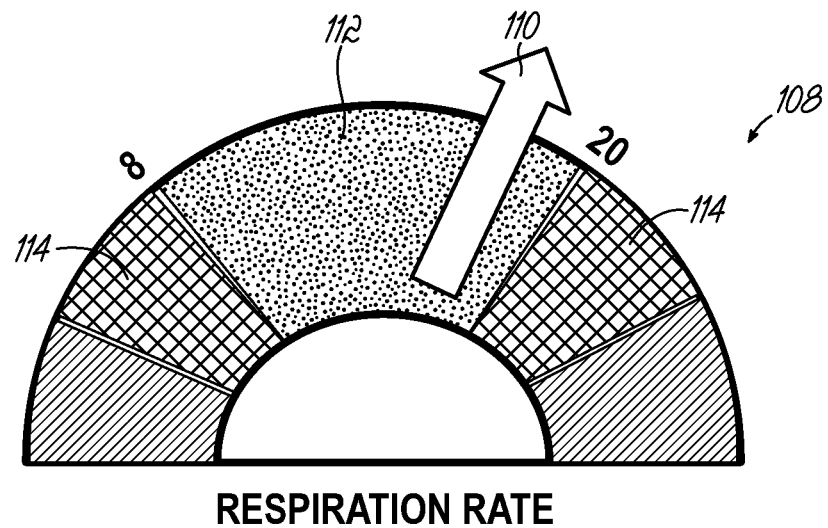
FIG. 22 is graphical representation of a respiration rate, as determined in accordance with an aspect of the invention.

The parameters and outputs that are the result of the system and method of the invention may be displayed in a number of different ways for providing a caregiver a real-time, graphical representation of the respiratory stress of a patient such as for characterizing various respiratory stress conditions. In one embodiment of the invention, the respiration rate, as well as the RSI parameter, is displayed. The parameter value may just be displayed, or the value in combination with a graphical component may be used. For example, as illustrated in FIG. 22, the respiration rate might be shown in a graded scale in a "speedometer" graphic, with numerical indications and a pointer 110 indicating the determined respiration rate. Also, the scale 108 might include various regions 112, 114 of different colors or patterns for indicating to a caregiver particular ranges of certain respiratory stress conditions 114, such as bradypnea and tachypnea, as well as an area where the respiration rate is considered "normal" 112.

Figure 23:
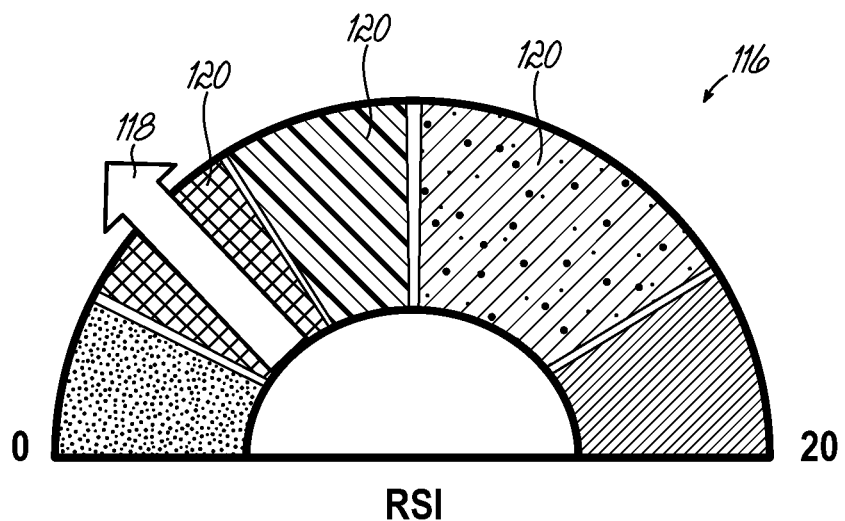
FIG. 23 is a graphical representation of a Respiratory Stress Index, as determined in accordance with one aspect of the invention.

In a similar fashion, as illustrated in FIG. 23, the RSI parameter may also be graphically illustrated on a suitable scale 116, having a pointer 118, and various different regions 120 that may be different colors or patterns or may otherwise be graphically distinguishable for providing certain regions that may indicate particular respiratory stress. Using the displayed information as illustrated in FIGS. 22 and 23, a caregiver may then make a possible diagnosis of the type of respiratory stress being experienced by the patient. Referring again to FIG. 1, as set forth in block 26, in addition to displaying the parameters, such as respiration rate and RSI, the derived parameters may be evaluated against thresholds and/or ranges (block 26). To that end, program flow may progress to process path D, as illustrated in FIG. 8. The respiration rate and RSI parameter are evaluated against a threshold and/or range for the purposes of recognizing and diagnosing respiratory stress and providing information and conditions for display and communication to a caregiver. For example, a threshold for normal breathing as illustrated by decision block 90 may be in the range of twelve to twenty breaths per minute. Similarly, an RSI index below one (1) may also be indicative of normal breathing conditions.

Figure 8:
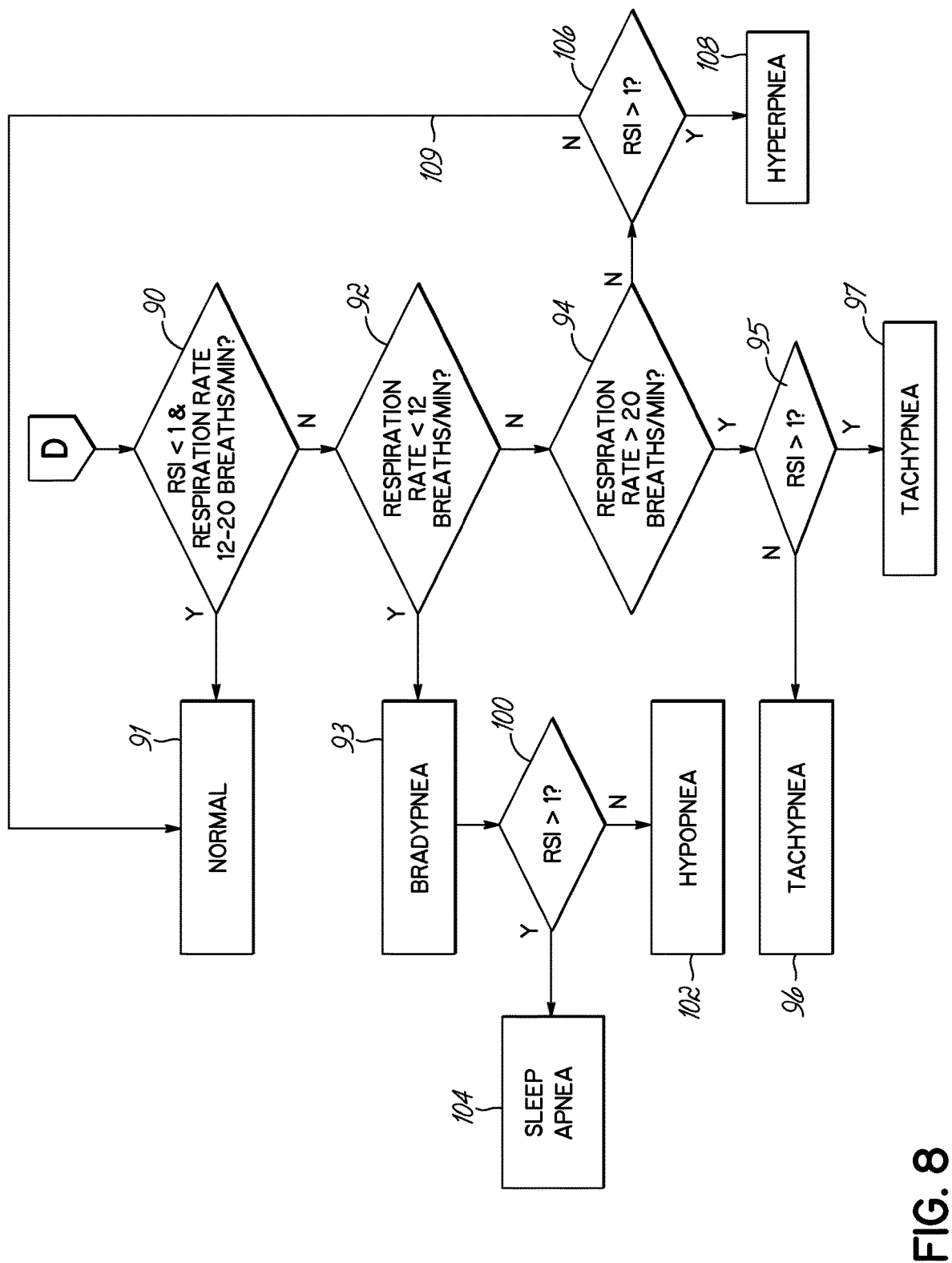
FIG. 8 is a flowchart of further signal processing flow in accordance with one embodiment of the invention.

The range set forth in FIG. 8 for normal breathing respiration rates is generally indicative of a healthy adult not considered an elderly adult exceeding sixty-five years of age. The range may be adjusted as appropriate, for the age of a patient, and therefore, in the decision block 90 of process D shown in FIG. 8, various different respiration rate ranges might be used depend on the age of the patient. Table 1 below gives various other respiration rates for different age patients.

TABLE 1

| Age | Breaths per minute |
| --- | --- |
| birth to 6 weeks | 30-40 |
| 6 months | 35-40 |
| 3 years | 20-30 |
| 6 years | 18-25 |
| 10 years | 17-23 |
| Adults | 12-18 |
| Elderly ≥65 years old | 12-28 |
| Elderly ≥80 years old | 10-30 |

In decision block 90, if the parameters RSI and respiration rate fall within the normal range and/or below a set threshold (e.g., RSI<1), an assessment of "Normal" for the patient might be provided and/or appropriately displayed, as illustrated in block 91. Such a normal condition might be displayed along with the display of respiration rate and RSI parameter, as illustrated in FIGS. 22 and 23, in the appropriate display mechanism, such as a screen of a tablet. If the current respiratory condition is not categorized as Normal, then it may be possible that the respiration rate falls outside of the normal range, either above or below, and/or the measured RSI parameter exceeds a noted threshold. In accordance with one embodiment of the invention, the respiration rate range set for each of the decision blocks shown in FIG. 8 might be set by a user. Similarly, the thresholds associated with RSI and other parameters in accordance with the invention might also be set by a user. Those ranges and thresholds might be set based upon a baseline category for a patient who, due to one or more medical conditions, may normally have what might otherwise be considered a respiratory stress condition.

If the condition of the patient is not normal for some reason based on RSI and/or respiration rate, program flow progresses to decision block 92 to determine if the respiration rate is below the endpoint of a defined range of normal, for example, below twelve breaths per minute. If so, as indicated by a "Yes" decision, the patient might be considered to be in a particular respiratory stress condition categorized as "bradypnea". Bradypnea is defined by respirations that are regular in rhythm but slower in rate than normal. Such a condition might be reported and/or displayed.

For further evaluation of the condition and stress, the RSI value may be evaluated as well in combination with the low respiration rate condition as reflected in block 100. If the RSI value is low and below the threshold, as reflected by a "No" decision in block 100, a further condition might be recognized. A low RSI value would indicate diminished depth and a condition known as "hypopnea" as reflected in block 102. Such a condition might be reported and/or displayed. If a low respiration rate is not indicated, such as the RSI value exceeds a threshold, as reflected by the "Yes" decision in block 100, the elevated RSI value may indicate a stress condition such as sleep apnea, for example, as reflected in block 104.

If the respiration rate is not low, as reflected in a "No" decision at block 92, the invention may determine if the respiration rate exceeds an upper limit of the defined range, for example, exceeding twenty breaths per minutes, as illustrated in block 94. If so, then particular respiratory stress associated with rapid breathing might be indicated and displayed. With such a rapid respiration rate, the RSI parameter then provides additional information regarding the particular respiratory stress based upon its comparison to a selected threshold.

In FIG. 8, that RSI threshold illustrated is one (1), as illustrated by decision block 95, but he RSI threshold might be set at other values as well. If the RSI value does not exceed the threshold, (e.g., 1) but there is rapid breathing based on the respiration rate, then, as indicated by the "No" decision in block 95, the respiratory stress condition of "tachypnea" might be indicated, as shown in block 96. If the RSI value that is determined in accordance with the invention exceeds the threshold, and there is a rapid respiration rate exceeding the upper limit of the defined normal range ("Yes" in decision block 95), the particular respiratory stress condition indicates it may be "tachypnea and hyperpnea", as illustrated by block 97. That information associated with any further processing as shown in FIG. 8 might also be reported and/or displayed along with the respiration rate and the RSI value along with the measured parameters and other outputs in accordance with the invention.

If the respiration rate is neither higher or lower than a normal rate, indicative of a "No" decision in block 94, there may still be a condition where respiratory stress exists, as the RSI value may have kept the condition from being indicated as normal. As such, in accordance with one aspect of the invention, RSI is still evaluated and reported and/or displayed. As shown in block 106, RSI values are compared against a threshold and if they exceed the threshold, then a respiratory stress condition, such as "hyperpnea" is indicated as shown in block 108. If the RSI value does not exceed the threshold, then the process may return as through path 109 for an assessment of normal, in which case the path would progress to a normal indication via block 91. Therefore, the various respiration rate and RSI conditions are further evaluated together in accordance with one feature of the invention to assist a caregiver in their assessment of a patient.

Therefore, in one aspect of the invention, the display of the derived respiration rate and RSI may be utilized by a caregiver to make a particular assessment, based upon their experience, of the respiratory stress associated with the patient, and their respiratory condition. Alternatively, through selected ranges and thresholds, the particular respiratory stress conditions or normal conditions might be diagnosed or suggested to the caregiver. As with the parameter values, the respiratory stress information may be reported and displayed, as illustrated by block 30 in FIG. 1. The process repeats during the course of the monitoring of a patient, as illustrated by loop path 32 in FIG. 1. As such, the patient undergoing a particular medical procedure or other stress that causes respiratory stress conditions, may be monitored during the process to determine the point at which respiratory stress conditions develop, indicating that an intervention is necessary to take care of the ongoing respiratory stress. As noted in the FIGS. 5-7B, additional information may be displayed and the respiratory stress index can indicate a significant increase and percent change in the baseline in a very short period of time (for example, several minutes). As such, the present invention provides a real-time analysis of developing respiratory stress conditions so that the caregiver can provide a suitable intervention before the situation gets any worse. Although the raw values of the respiration rate and RSI values are shown in FIGS. 22-23, the percent changes of those values might also be calculated and displayed from a baseline value.

Figure 9A:
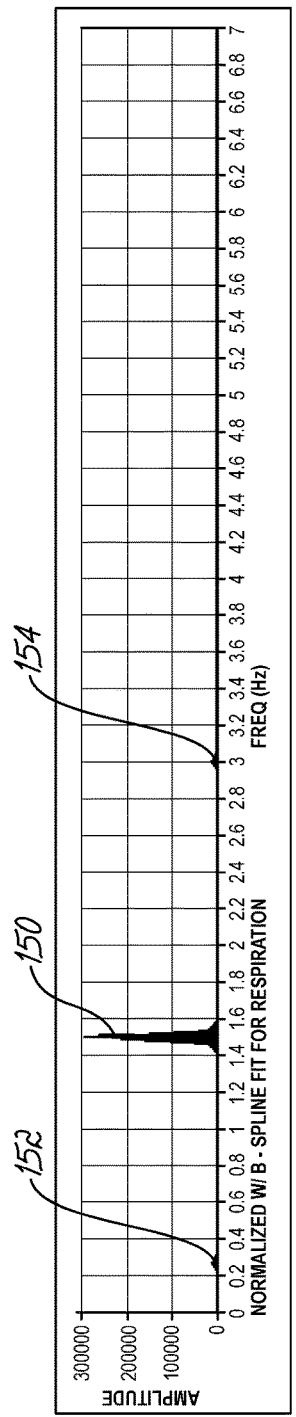
FIGS. 9A-9C are graphical representations of frequency-domain and time-domain signals reflective of biological signals of a person that are analyzed in accordance with the present invention and reflect normal respiration with FIG. 9A being a frequency-domain representation of a PPG signal, and FIG. 9B being a normalized time-domain representation of a PPG signal and FIG. 9C being a raw PPG signal

FIGS. 9A-21B provide various charts illustrating the frequency analysis and time-domain analysis made of a PPG signal for various patents in accordance with aspects of the invention for displaying the defined parameter of respiratory stress index, or RSI, respiratory rate, and other valuable information. Referring to FIGS. 9A and 10A, a frequency analysis is illustrated for two patients in accordance with the invention (See FIG. 3) and indicates significant spectral power and a peak 150 around 1.5 Hz as a pulse rate frequency. The peak 152 around 0.3 hertz is indicative of the respiration rate frequency and translates approximately into eighteen breaths per minute. A pulse rate harmonic is also indicated by the peak 154 in FIG. 9A. Similarly, in FIG. 10A, significant spectral power is indicated at the pulse rate peak 150, with respiration rate indicated at peak 152 and a pulse rate harmonic at 154.

Figure 9B:
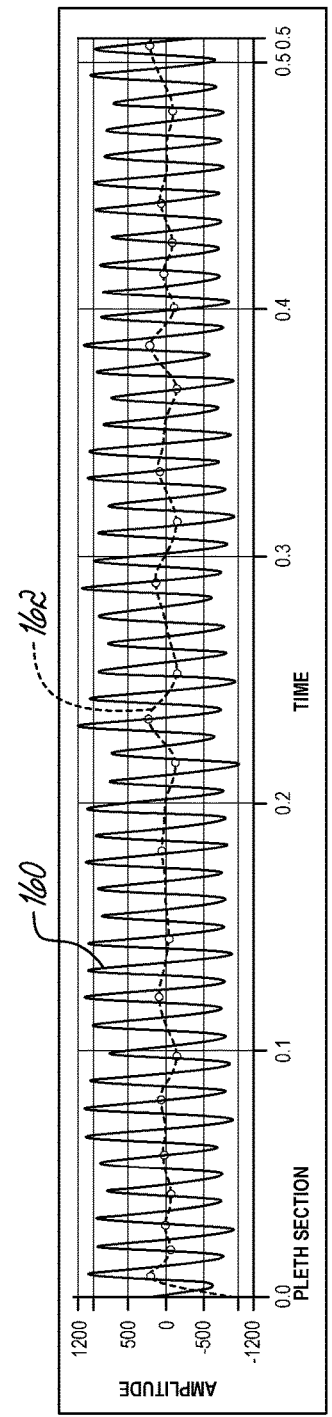
Figure 9C:
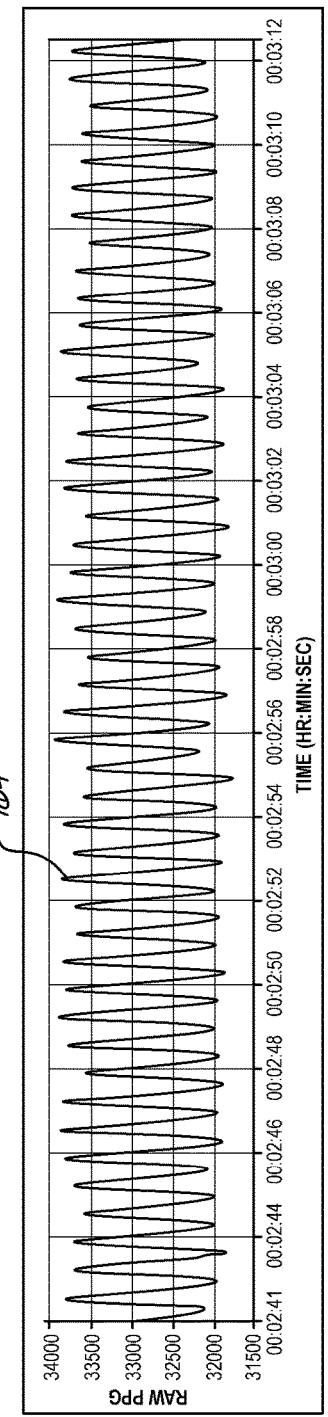
Figure 10A:
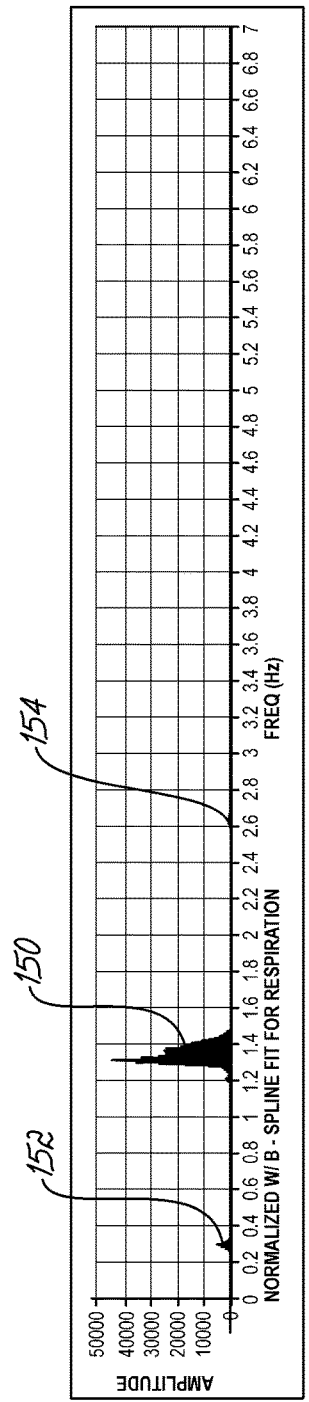
FIGS. 10A-10C are similar representations as in FIGS. 9A-9C for another different person.
Figure 10B:
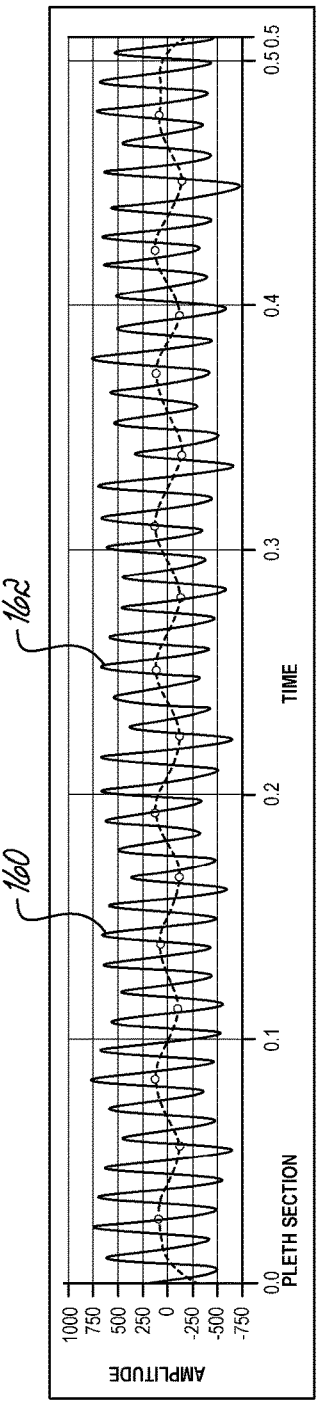
Figure 10C:
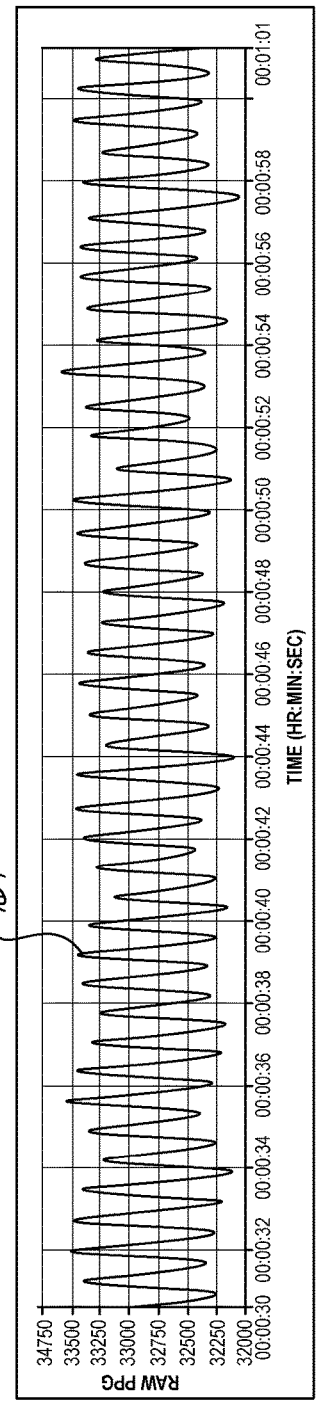

FIGS. 9B and 10B indicate a normalized PPG or "pleth" signal 160, with an overlay of the B-spline fit respiration curve 162, in accordance with the invention. FIGS. 9C and 10C illustrate the raw PPG signal 164, which is obtained from a patient using an appropriate sensor. As may be seen, the respiratory component 162 does not contribute significantly to the cardiac signal, and there is not a significant correlation between the PPG signal curve 160 and the B-spline fit curve 162. As such, the $r^2$ value is somewhat low, and below one (1), thus, indicating normal respiratory functions and effectively no significant respiratory stress, in accordance with the invention.

Figure 11A:
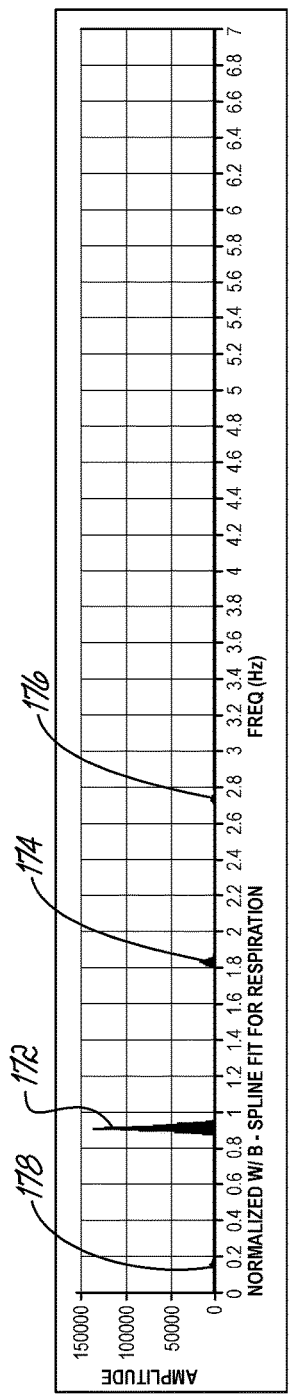
FIGS. 11A-11C are graphical representations of frequency-domain and time-domain signals reflective of biological signals of a person similar to the time-domain and frequency-domain FIGS. 9A-9C that are analyzed in accordance with the present invention and reflect a respiratory stress condition.

FIGS. 11A-12C show signals indicative of a respiratory stress condition that might be categorized as bradypnea, which is an abnormally slow respiration rate with normal rhythm. For example, as illustrated in FIG. 11A, from a frequency analysis of the raw PPG signal 170 set forth in FIG. 11C, the spectral peak for the pulse rate is illustrated at 172 and harmonics at 174, 176 and are above the respiration rate peak 178. The respiration rate peak at the indicated frequency translates to a respiration rate of approximately 8-9 breaths per minute, which is certainly below what is considered normal for an adult (see Table 1). As such, the "Yes" decision in block 92 would indicate a condition of bradypnea (block 93).

Figure 11B:
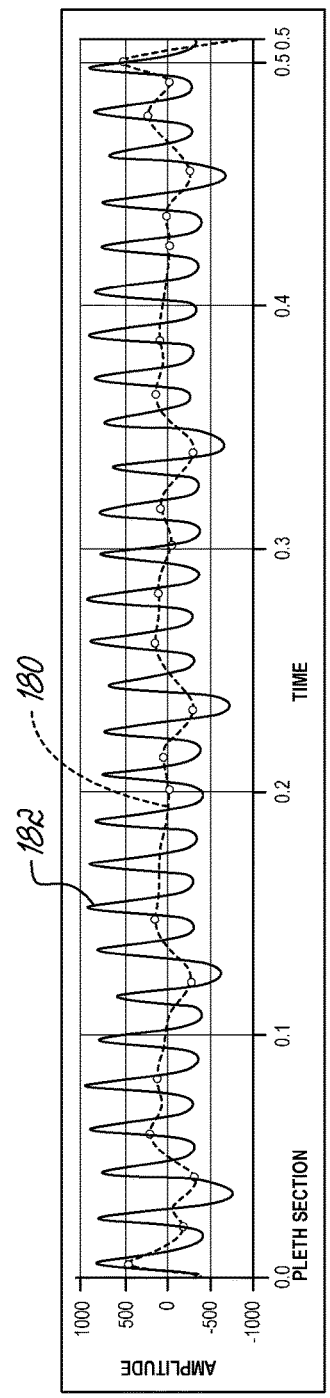
Figure 11C:
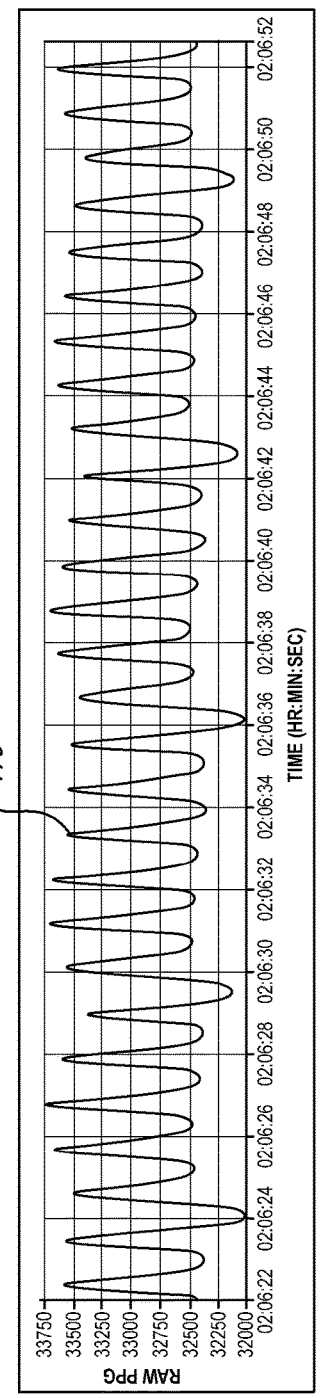

Further signal processing can be done, even in a bradypnea condition as shown in FIG. 8. For example, the RSI value could be evaluated as well to determine other conditions. For example, as illustrated in FIG. 11B, there is not a significant correlation between the B-spline fit curve 180 and the pleth or PPG signal curve 182 that has been normalized as illustrated in FIG. 11B. As such, the correlation coefficient $r^2$ for the respiratory component of the overall pleth/PPG signal is still low, yielding an RSI value that is also low and below the threshold of one (1). As such, based on the signal processing as shown in FIG. 8 and block 100, a decision of "No" with respect to the RSI exceeding the threshold a respiratory condition may be further categorized as hypopnea, defined as a diminished depth and rate.

Figure 12A:
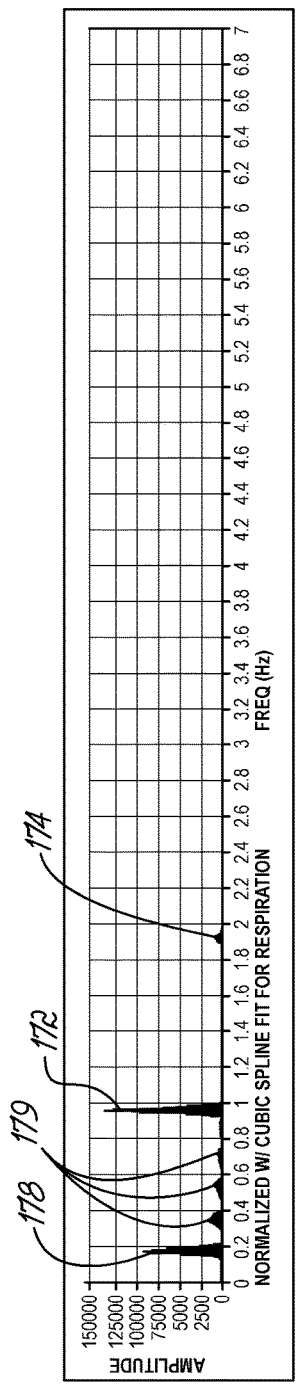
FIGS. 12A-12C are graphical representations of frequency-domain and time-domain signals reflective of biological signals of a person similar to the time-domain and frequency-domain FIGS. 9A-9C that are analyzed in accordance with the present invention and reflect a respiratory stress condition.
Figure 12B:
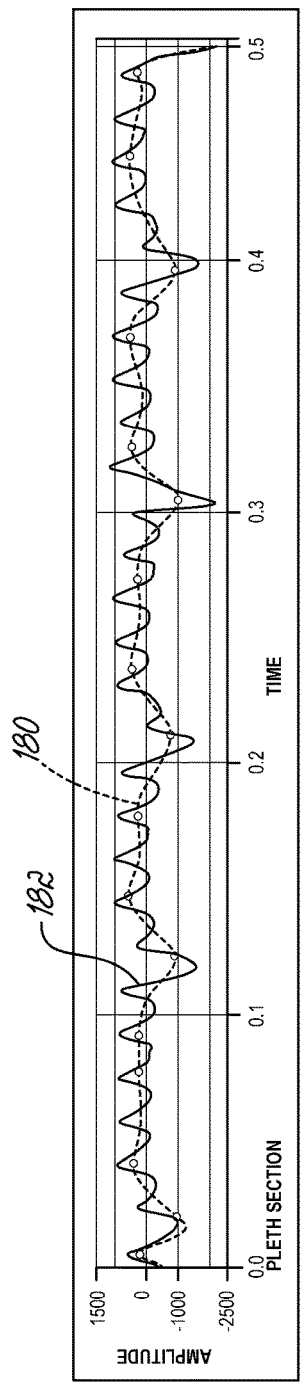
Figure 12C:
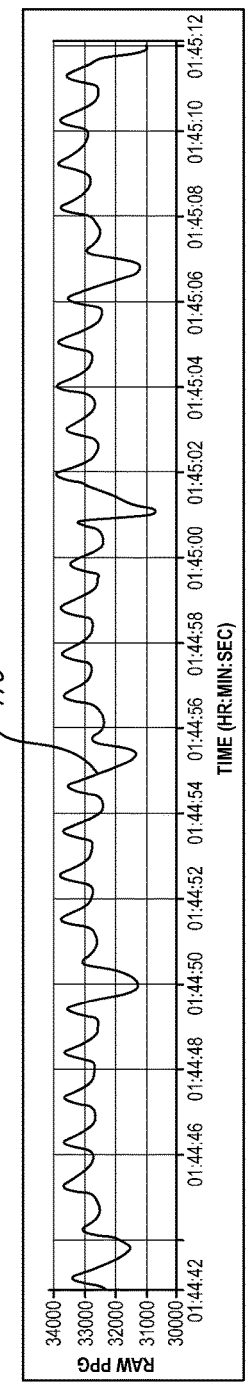

However, even with bradypnea indicated by the lower than normal respiration rate, the further signal analysis might show that respiratory stress is evident as well in that condition. As illustrated in FIG. 12A, from a frequency analysis of the raw PPG signal 170 set forth in FIG. 12C, the spectral peak for the respiration rate 178 and its multiple harmonics at 179 demonstrates significant content nearly equivalent to the pulse rate peak at 172 and the harmonic at 174. FIG. 12B also illustrates a significant correlation between the B-spline fit curve 180 and the pleth or PPG signal curve 182. As such the correlation coefficient $r^2$ for the respiratory component of the overall pleth/PPG signal is high, for example around 0.5814. This yields an RSI value that is higher (e.g., 10.4) and above the threshold of one (1), thus yielding a "Yes" in decision block 100. Based on the further analysis and processing of the signals and the RSI values, as illustrated in FIG. 8, this allows additional characterization of the respiratory stress which could be indicative of a sleep apnea disorder, such as central or obstructive sleep apnea, for example. (block 104)

The signal graphs set forth in FIGS. 13A-13C and 14A-14C are indicative of a respiratory stress that might be categorized as tachypnea. The frequency analysis spectral peaks and harmonics 190, 192 in FIGS. 13A, 14A reflective of the pulse rate as determined from the PPG signal of FIG. 13C still indicate dominant spectral energy within the cardiac component of the PPG signal. However, the spectral peak 194 indicative of the respiration rate indicates a rate of approximately twenty-seven breaths per minute, which is significantly increased and above what might be considered the normal range as set forth in FIG. 8. However, because the cardiac component is still dominant within the PPG signal, the B-spline fit curve 198 of FIGS. 13B, 14B does not show a strong correlation with the pleth/PPG signal 196. As such, the correlation coefficient $r^2$ remains somewhat low, as does the total spectral power of the respiratory component 194 in the PPG signal. Accordingly, the RSI value may not exceed the noted threshold, as set forth in FIG. 8, thus, indicating a respiratory stress that might be categorized as tachypnea.

Figure 15A:
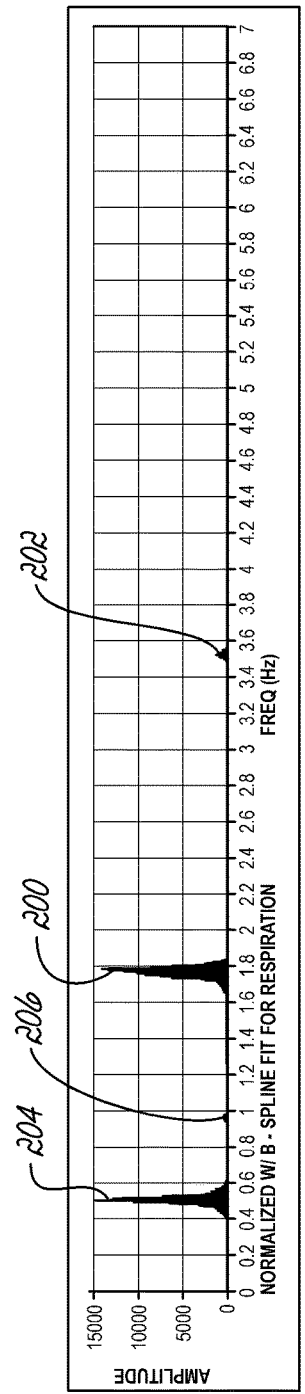
FIGS. 15A-15C are graphical representations of frequency-domain and time-domain signals reflective of biological signals of a person similar to the time-domain and frequency-domain FIGS. 9A-9C that are analyzed in accordance with the present invention and reflect another respiratory stress condition and FIGS. 16A-16C are similar representations as in FIGS. 15A-15C for another different person.
Figure 15B:
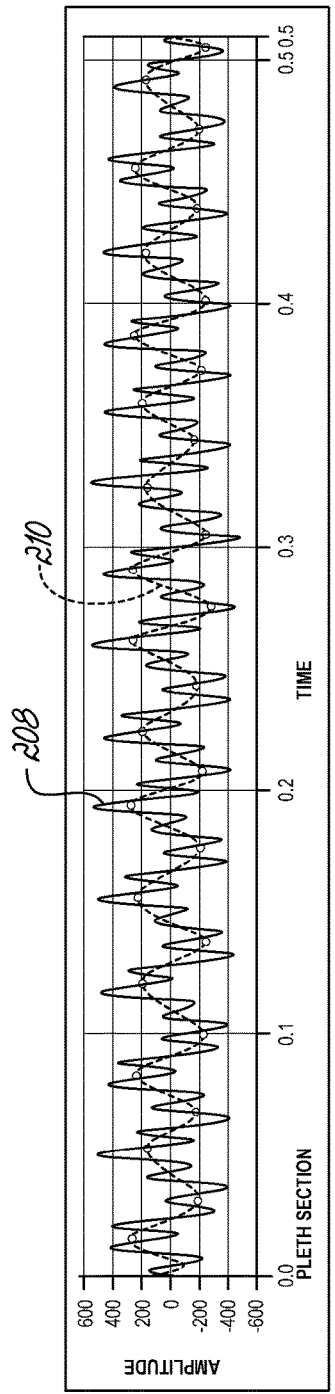
Figure 15C:
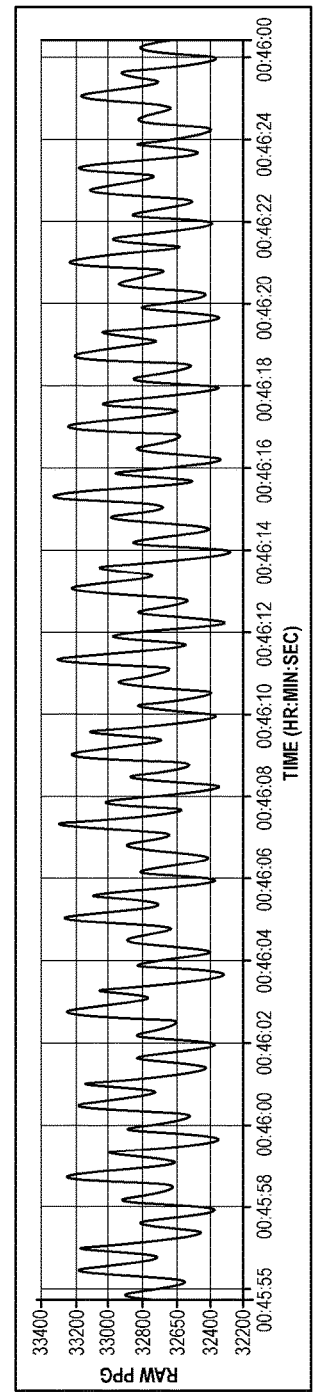
Figure 16A:
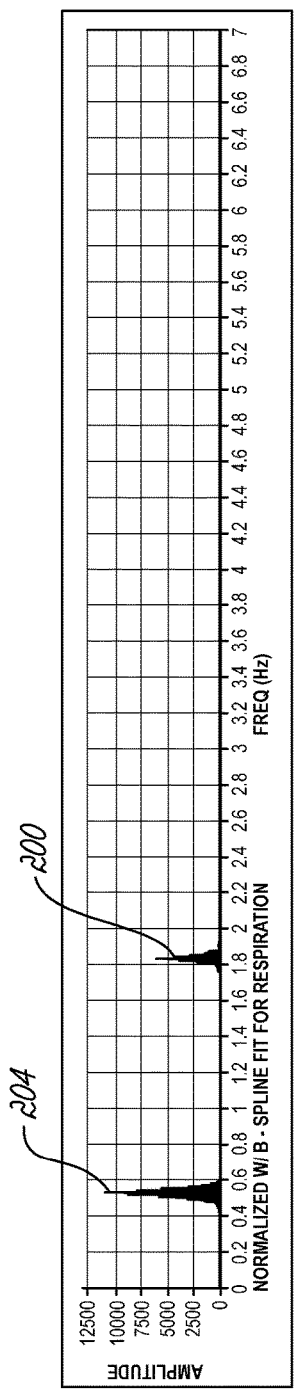
Figure 16B:
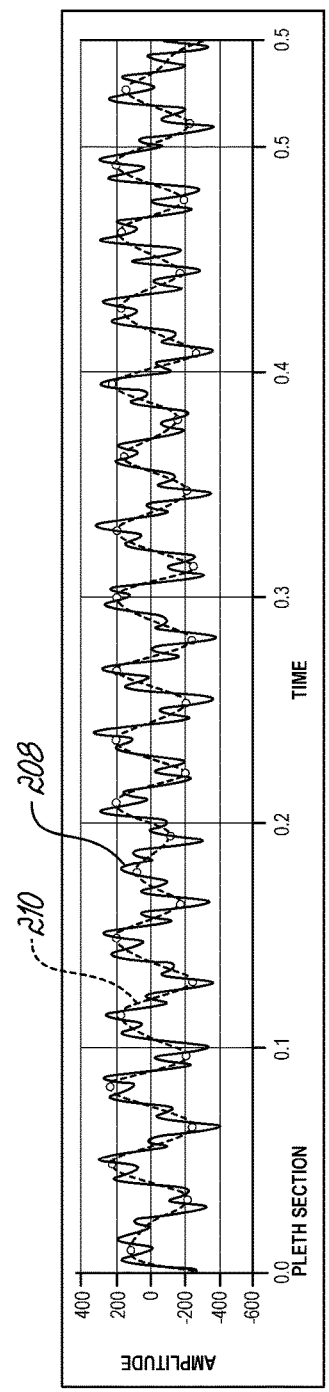
Figure 16C:
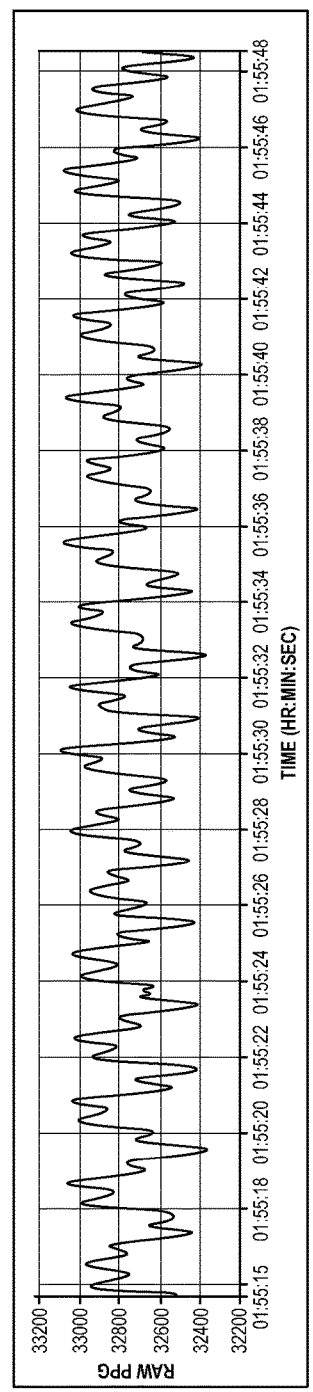

FIGS. 15A-15C and 16A-16C illustrate examples of a respiratory stress condition that might be categorized as tachypnea with hyperpnea. Such a condition is reflective of the respiratory component generally overtaking the cardiac component within a PPG signal, such that a significant amount of spectral energy is associated with a respiratory component, and there is a strong correlation (e.g., high $r^2$). As illustrated in FIGS. 15C and 16C, the PPG signal is significantly distorted from what might be considered a normal PPG signal. That is because the respiratory component begins to dominate the PPG signal, as determined using the invention. As illustrated in FIGS. 15A and 16A, the spectral peaks and harmonics at 200, 202 are indicative of the pulse rate component of the PPG signal and are matched or exceeded by the spectral components 204, 206 indicative of the respiratory rate and harmonics associated therewith. As illustrated in FIG. 15A, 15B, spectral peak 204 is generally close to or equal to spectral peak 200 in amplitude and power. In FIG. 16A, the spectral peak 204 associated with the respiratory component significantly exceeds peak 200 in amplitude and power. Furthermore, the frequency of the respiratory spectral peaks 204 is indicative of an abnormally elevated respiration rate of approximately 30-32 breaths per minute. Furthermore, as illustrated in FIGS. 15B and 16B, there is significant or strong correlation between the PPG signal curve 208 and the B-spline fit curve 210, thus indicating an $r^2$ value approaching closer to one. As such, the RSI associated with the tachypnea with hyperpnea condition as illustrated in FIGS. 15A-15C, 16A-16C will be significantly higher than the threshold, as noted in FIG. 8, thus indicating a respiratory stress that may be categorized as tachypnea with hyperpnea.

Accordingly, the present invention may be utilized to provide a significant assessment and characterization of respiratory stress in a patient for providing the caregiver the necessary information and tools so that they might provide an appropriately planned intervention when such respiratory stress appears, and stress conditions reach undesirable levels. Although certain examples illustrated herein use a threshold value of one (1), other threshold values might be used and set by a user. Furthermore, while certain stress conditions are indicated by name, other conditions might be indicated based on the signal processing and other processing of the invention. Therefore, the invention is not dependent on a particular threshold for the RSI value as determined or for a specific name given to the stress condition determined.

Figure 17A:
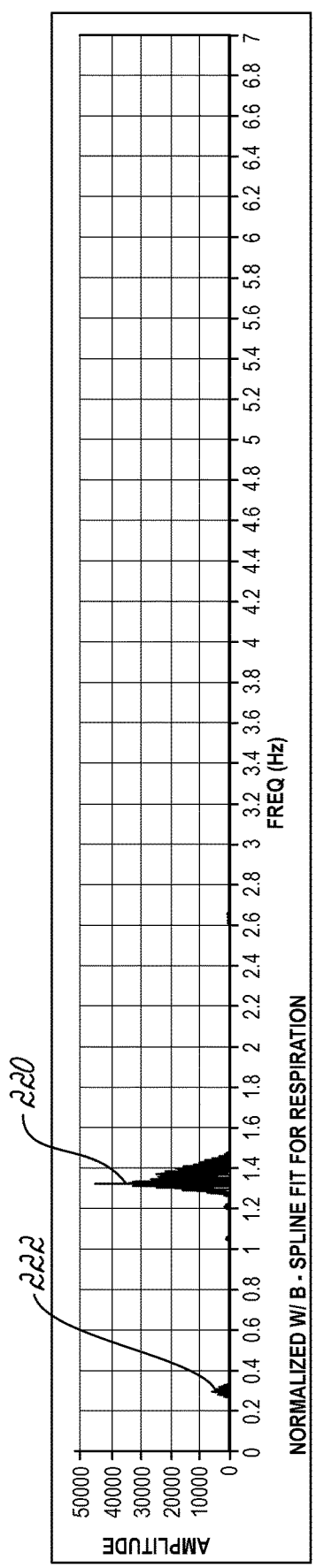
FIGS. 17A-17B are graphical representations of frequency-domain and time-domain representations of biological signals for a person progressing through a medical procedure and illustrating the onset of a respiratory stress condition and each of the progressing representations of FIGS. 18A-18B, 19A-19B, 20A-20B, and 21A-21B are similar to the frequency-domain and time-domain signals of FIGS. 17A-17B, just further along in a progression of a the medical procedure.
Figure 17B:
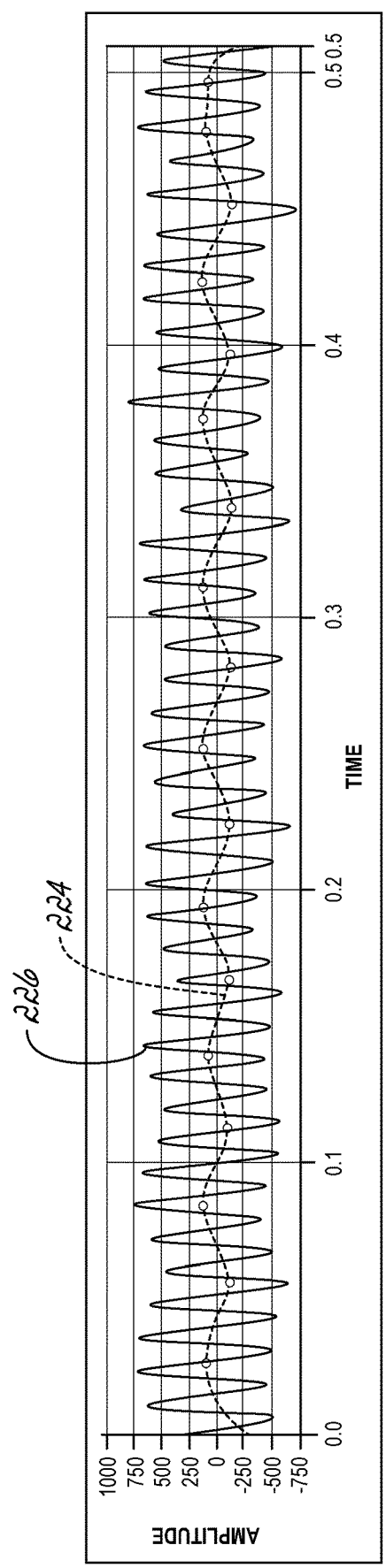

The present invention can find particular use in real-time monitoring and characterization of respiratory stress and other respiratory conditions for patients undergoing a particular medical procedure that may introduce stress into the cardiovascular and respiratory systems. One non-limiting example noted herein is a hemodialysis process. FIGS. 17A-21B provide a series of figures indicating varying respiratory conditions and respiratory stress occurring for a patient during the progression of a hemodialysis process. Turning to FIG. 17A, a frequency-domain graph of the amplitude of spectral elements of the time-domain PPG signal in FIG. 17B is illustrated. Each of the other signals 18A-18B, 19A-19B, 20A-20B, and 21A-21B are similar to the frequency-domain and time-domain signals of FIGS. 17A-17B, just further along in a progression of a hemodialysis process. FIGS. 17A and 17B are indicative of approximately six minutes into a hemodialysis process. The cardiac component peak 220 exceeds that respiratory component peak 222 that yields a respiration rate of around 18-20 breaths per minute, and there is not significant correlation between the B-spline fit curve 224 of the respiratory component and the PPG signal 226. As such, respiration is normal.

Figure 18A:
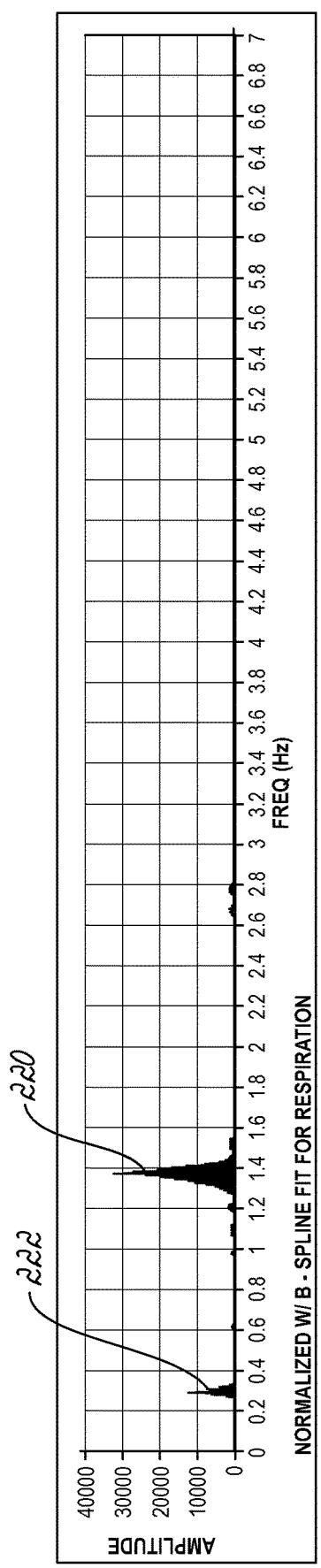
Figure 18B:
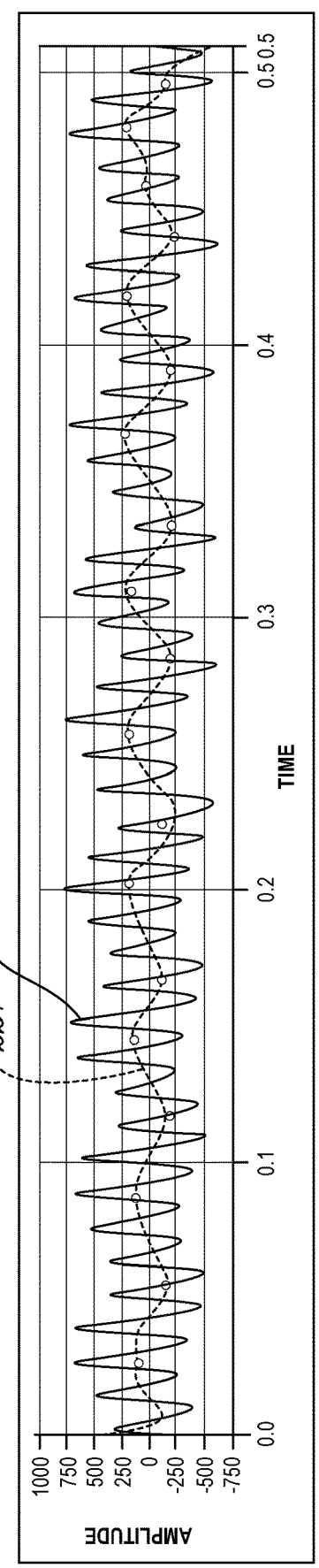

FIGS. 18A and 18B are indicative of the progress thirty-five minutes into a hemodialysis process. As may be seen in FIG. 18A, the respiratory component spectral peak is starting to increase in amplitude at a similar rate as FIGS. 17A-17B, while curve 224 is beginning to become a more significant component of the PPG signal. Generally, after thirty-five minutes, the derived cardiorespiratory ratio is around 27, and an $r^2$ value of 0.16 yields an RSI value of approximately 4.3.

Figure 19A:
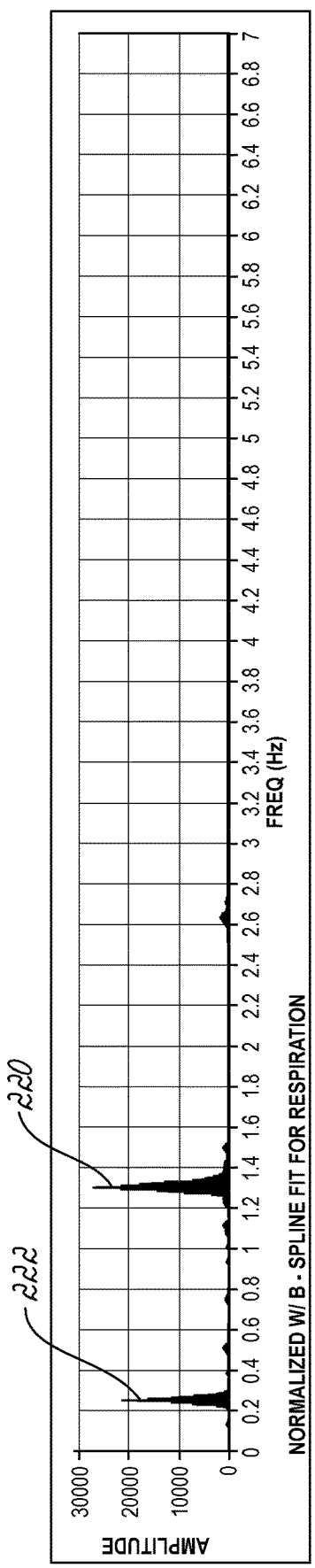
Figure 19B:
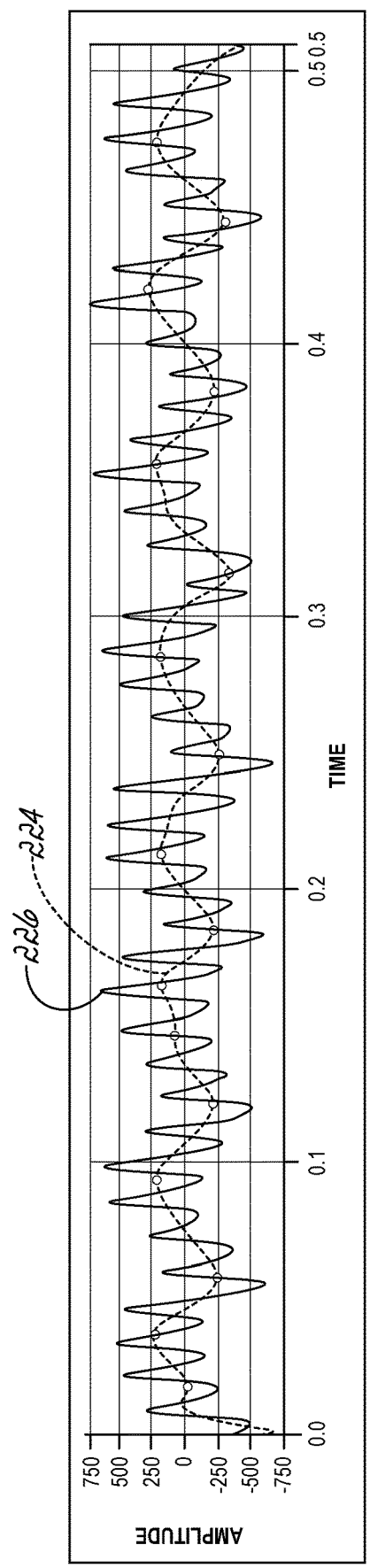

FIGS. 19A-19B are indicative of the respiratory condition ninety minutes into the hemodialysis process. As may be seen in FIG. 19A, the respiratory component spectral peak 222 is gaining significantly in amplitude which is reflected in a decrease in the amount of energy associated with the cardiac component peak 220. At the same time, the respiratory component curve 224 is beginning to have a greater influence in the PPG signal 226. The signals of FIGS. 19A, 19B yield a cardiorespiratory ratio of around 45.8, and an $r^2$ value of around 0.325 yielding a derived RSI parameter value of around 7.8, in accordance with the invention.

Figure 20A:
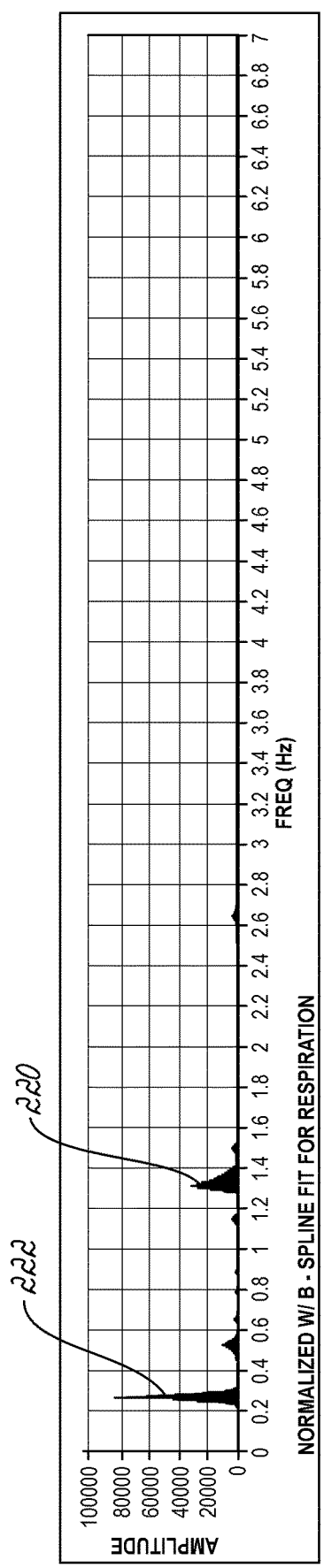
Figure 20B:
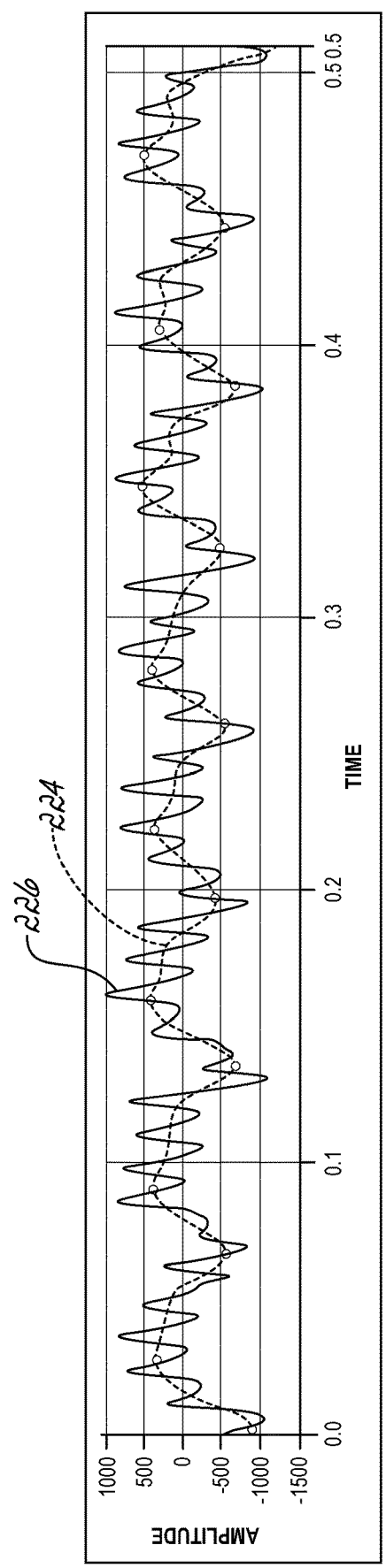

Turning now to FIGS. 20A and 20B, the frequency analysis is indicative of a respiratory condition wherein the respiratory component begins to dominate the PPG signal, as indicated by the increase of the amplitude of the respiratory component peak 222 versus the pulse rate component peak 220. Furthermore, there is greater correlation between curves 224 and 226, as illustrated in FIG. 20B. FIGS. 20A and 20B are indicative of a patient that is 103 minutes into a dialysis process. In accordance with the invention, the system indicates a cardiorespiratory ratio of around 74.2, and an $r^2$ value of 0.57 providing an RSI measurement of approximately 13.1.

Figure 21A:
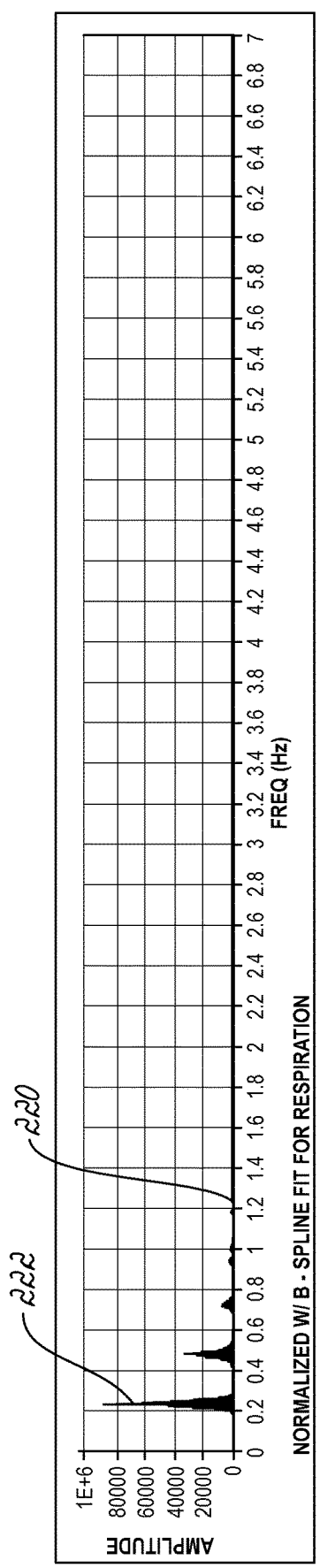
Figure 21B:
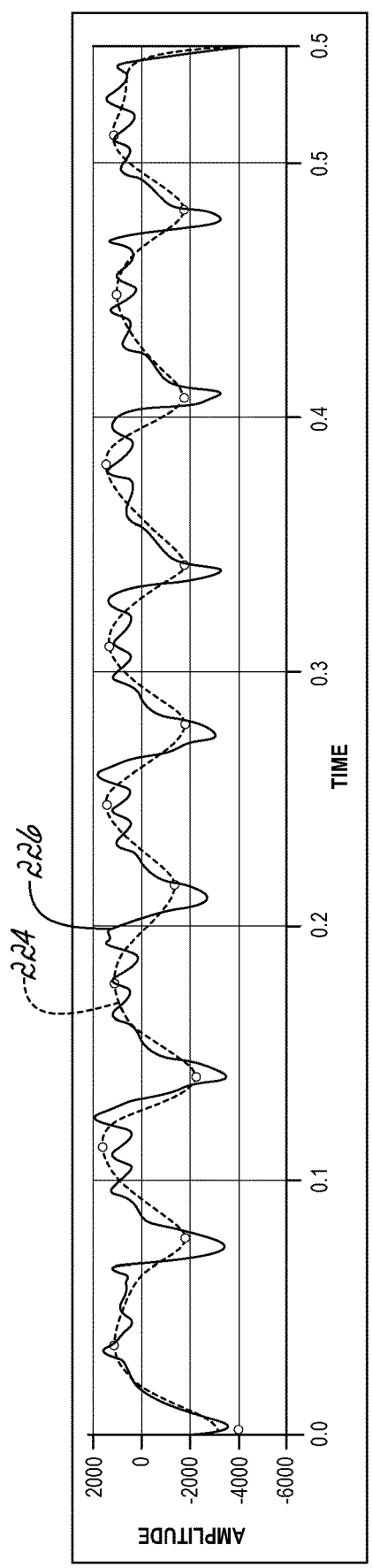

FIGS. 21A-21B are illustrative of a patient 114 minutes into the dialysis process, wherein the respiratory component has become significantly dominant within the PPG signal showing significant spectral energy in respiratory component peak 222 and associated harmonics versus the cardiac component peak 220. Furthermore, as illustrated in FIG. 21B, there is significant correlation between the respiratory curve 224 and the PPG signal 226 indicating that the respiration signal is dominating the PPG signal. The respiration rate is normal but such a condition yields the cardiorespiratory ratio of around 98.2, and a correlation coefficient $r^2$ of around 0.743. The RSI value is a significantly high 17.25, and thus indicative of hyperpnea (See FIG. 8).

In accordance with another aspect of the invention, as noted herein, the detected respiratory stress may be detected and indicated in accordance with the invention even if the respiratory rate is in the "normal" range. Therefore, the present invention is not limited to those instances wherein the respiratory rate is outside a normal range. In accordance with the invention, the indication of Respiration Rate and RSI is provided as shown in FIGS. 22-23 in order to reflect various stress conditions as well as the respiration rate independent of each other. Therefore, while certain stress conditions may be accompanied by a respiration rate outside the normal range and that information may be used to classify various conditions, in accordance with one feature of the invention, the determination of a stress condition through the evaluation of RSI and other signal processing is not limited to abnormal respiration rates as shown in FIG. 8.

Figure 24:
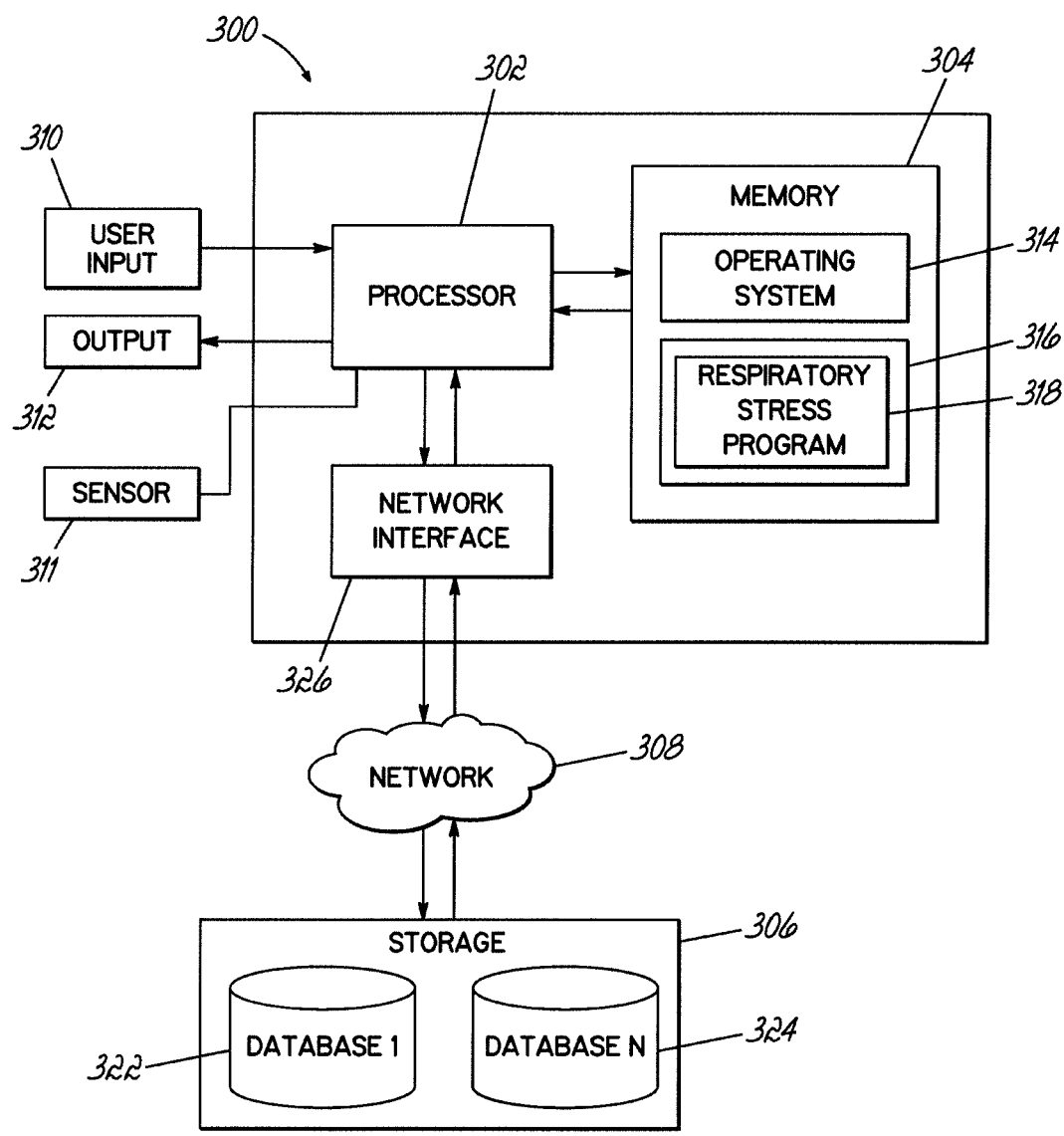
FIGS. 24-28 are schematic diagrams of exemplary hardware systems for implementing embodiments of the invention.

As noted herein, the invention may be implemented in a suitable computer device, such as a tablet device, such as the device used to implement the CVInsight® System available from Intelomed, Inc. However, other devices or systems may be used. For example, FIG. 24 illustrates an exemplary hardware and software environment for an apparatus 300 suitable for implementing the process and system consistent with the invention. For the purposes of the invention, apparatus 10 may represent practically any computer, computer system, or programmable device, mobile device e.g., portable tablets and devices, handheld devices, network devices, mobile phones multi-user or single-user computers, desktop computers, etc. Apparatus 300 will hereinafter be referred to as a "computer" although it should be appreciated that the term "apparatus" may also include other suitable programmable electronic devices.

Computer 300 typically includes at least one processor 302 coupled to a memory 304. Processor 302 may represent one or more processors (e.g. microprocessors), and memory 304 may represent the random access memory (RAM) devices comprising the main storage of computer 300, as well as any supplemental levels of memory, e.g., cache memories, non-volatile or backup memories (e.g. programmable or flash memories), read-only memories, etc. In addition, memory 304 may be considered to include memory storage physically located elsewhere in computer 300, e.g., any cache memory in a processor 302, as well as any storage capacity used as a virtual memory, e.g., as stored on a mass memory storage device or system 306 or another computer that may be coupled to computer 300, such as through a network 308. The mass storage system 306 may include cloud storage or other appropriate remote storage components that may support one or more (1-n) databases 322, 324. The mass storage system might be accessed through network 308.

Computer 300 also typically receives a number of inputs and outputs for communicating information externally. For interface with a user or operator, computer 10 typically includes one or more user input devices 310 (e.g., a touchscreen, camera, microphone, keyboard, mouse, trackball, joystick, keypad, stylus, among others). In accordance with one embodiment of the invention, the input device is a sensor 311 for detecting a biological signal, such as a PPG signal. Computer 300 may also include one or more output or display elements 312 (e.g., a screen, separate monitor or display, speaker, among others). The interface to computer 300 may also be through an external terminal connected directly or remotely to computer 300, or through another computer communicating with computer 300, such as via a network 308.

Computer 300 operates under the control of an operating system 314, and executes or otherwise relies upon various computer software applications, components, programs, objects, modules, data structures, etc 316. (e.g. Respiratory Stress application 318). Application 318, for example, may provide the various processing steps set forth herein for characterizing respiratory stress. Computer 300 communicates on the network 308 through a suitable wired or wireless network interface 326, such as a WIFI link. The computer 300 may be coupled with appropriate storage through network interface 326 and network 308.

In general, the routines executed to implement the embodiments of the invention, whether implemented as part of an operating system or a specific application, component, program, object, module or sequence of instructions will be referred to herein as "computer program code", or simply "program code". The computer program code typically comprises one or more instructions that are resident at various times in various memory and storage devices in a computer, and that, when read and executed by one or more processors or processing units in a computer, causes that computer to perform the steps necessary to execute steps or elements embodying the desired functionality of various aspects of the invention. Moreover, while the invention has and hereinafter will be described in the context of fully functioning computers and computer systems, those skilled in the art will appreciate that the various embodiments of the invention are capable of being distributed as a program product in a variety of forms. The invention applies equally regardless of the particular type of computer readable storage media used to actually carry out the distribution, e.g., physical, recordable type storage media such as volatile and non-volatile memory devices, portable or thumb drives and various disks, or remote storage, such as on a server or cloud storage, that may be accessed via a network connection. Furthermore, since functionality of the system might be distributed between various components, such as servers, mobile devices and other components, the invention is not limited to specific components handling specific functions.

Such computer readable media may include computer readable storage media and communication media. Computer readable storage media is non-transitory in nature, and may include volatile and non-volatile, and removable and non-removable media implemented in any method or technology for storage of information, such as computer-readable instructions, data structures, program modules or other data. Computer readable storage media may further include RAM, ROM, erasable programmable read-only memory (EPROM), electrically erasable programmable read-only memory (EEPROM), flash memory or other solid state memory technology, CD-ROM, DVD, or other optical storage, magnetic cassettes, magnetic tape, magnetic disk storage or other magnetic storage devices, or any other medium that can be used to store the desired information and which can be accessed by a computer or other device. Communication media may embody computer readable instructions, data structures or other program modules. By way of example, and not limitation, communication media may include wired media such as a wired network or direct-wired connection, and wireless media such as acoustic, RF, infrared and other wireless media. Combinations of any of the above may also be included within the scope of computer readable media.

In addition, various program code described hereinafter may be identified based upon the application or software component within which it is implemented in specific embodiments of the invention. However, it should be appreciated that any particular program nomenclature that follows is merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the invention is not limited to the specific organization and allocation of program functionality described herein.

Those skilled in the art will recognize that the exemplary environment illustrated in FIG. 24 is not intended to limit the present invention. Indeed, those skilled in the art will recognize that other alternative hardware and/or software environments may be used without departing from the scope of the invention.

FIGS. 25-28 illustrate various other possible and non-limiting embodiments of a computer system 300 in which embodiments of the present invention may be implemented. Various embodiments of a system 300 for detecting respiratory stress include a sensor 311 that acquires a biological signal, a processor 302 that includes one or more appropriate software modules 340, 342, 344 residing in memory for processing and analyzing the sensor signal, and an interface module 346 that generates appropriate output parameter 350, as discussed herein. In the embodiment illustrated in FIG. 25, the sensor 311 is in communication with, via a wireline or wireless connection, the processor 302 that is external to the sensor 10. The system 300 may further include appropriate memory storage 306, as noted, that might be in the computer system or device or remotely coupled through a network interface (not shown in FIG. 25).

As described herein, the sensor for detecting a biological signal may be any invasive or non-invasive device that includes appropriate circuitry to acquire a biological signal. The sensor may be coupled with a device in a wired or wireless connection for further processing of any signals, such as biological signals, produced by the sensor.

Figure 25:
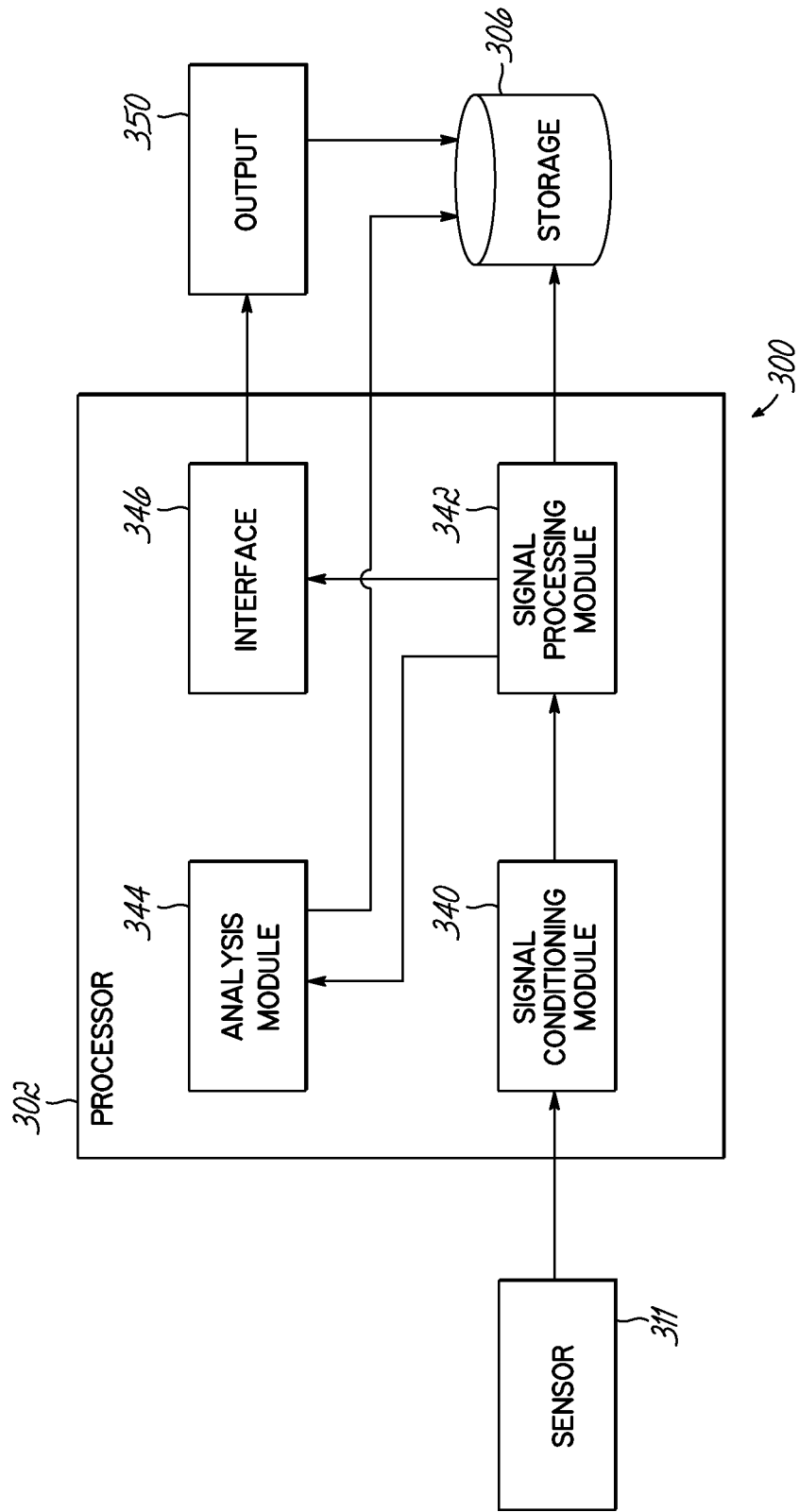
Figure 26:
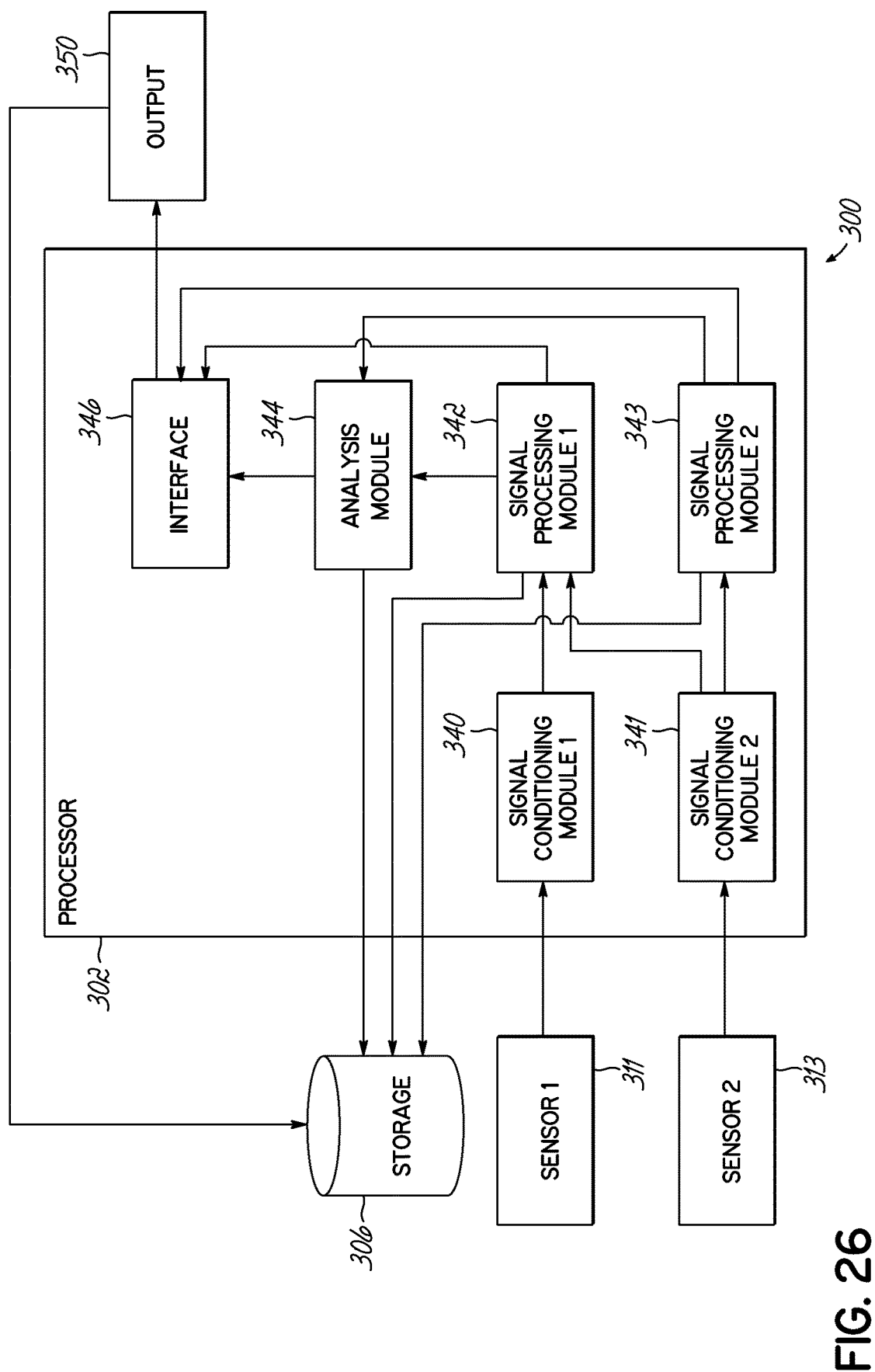
Figure 27:
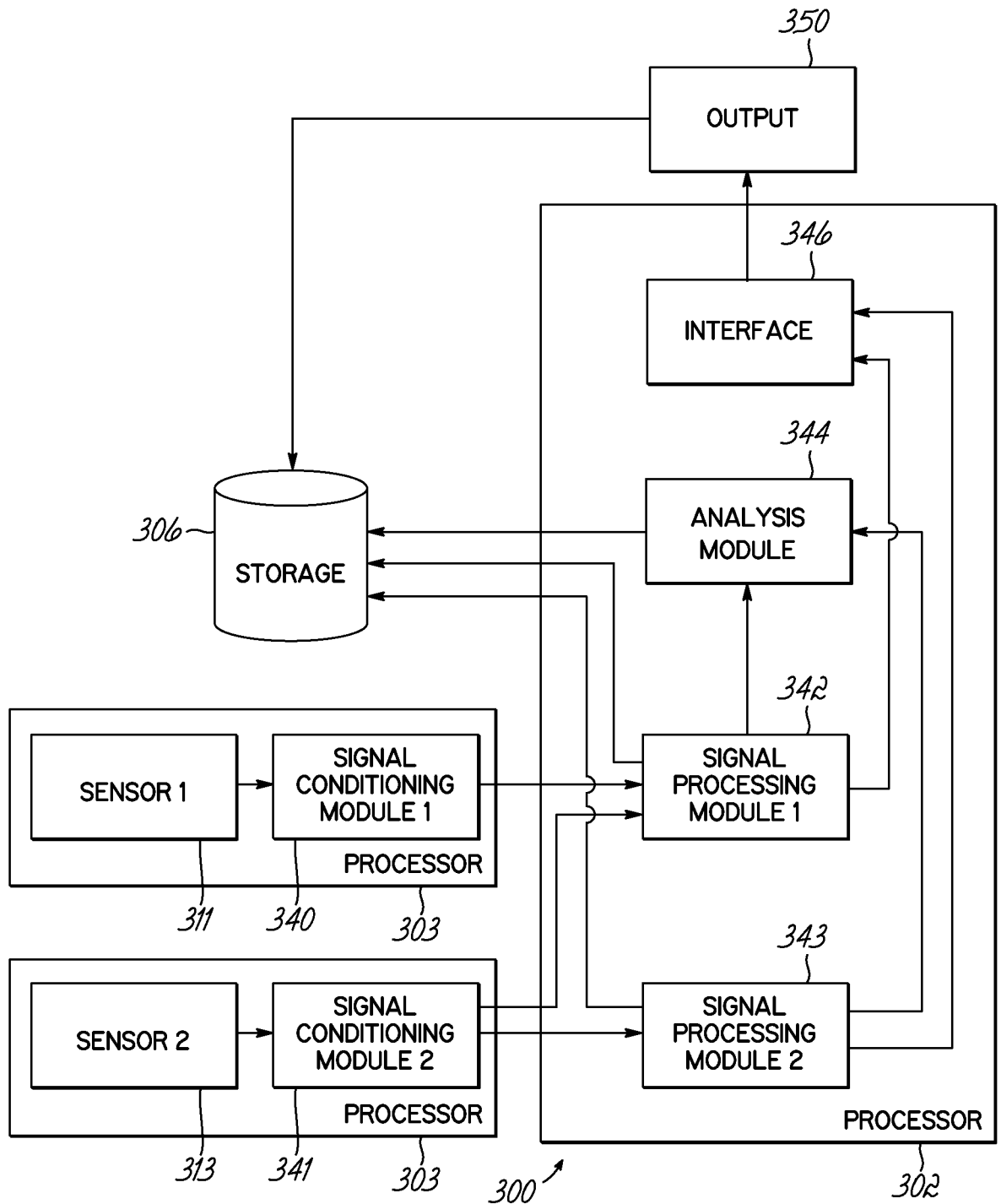
Figure 28:
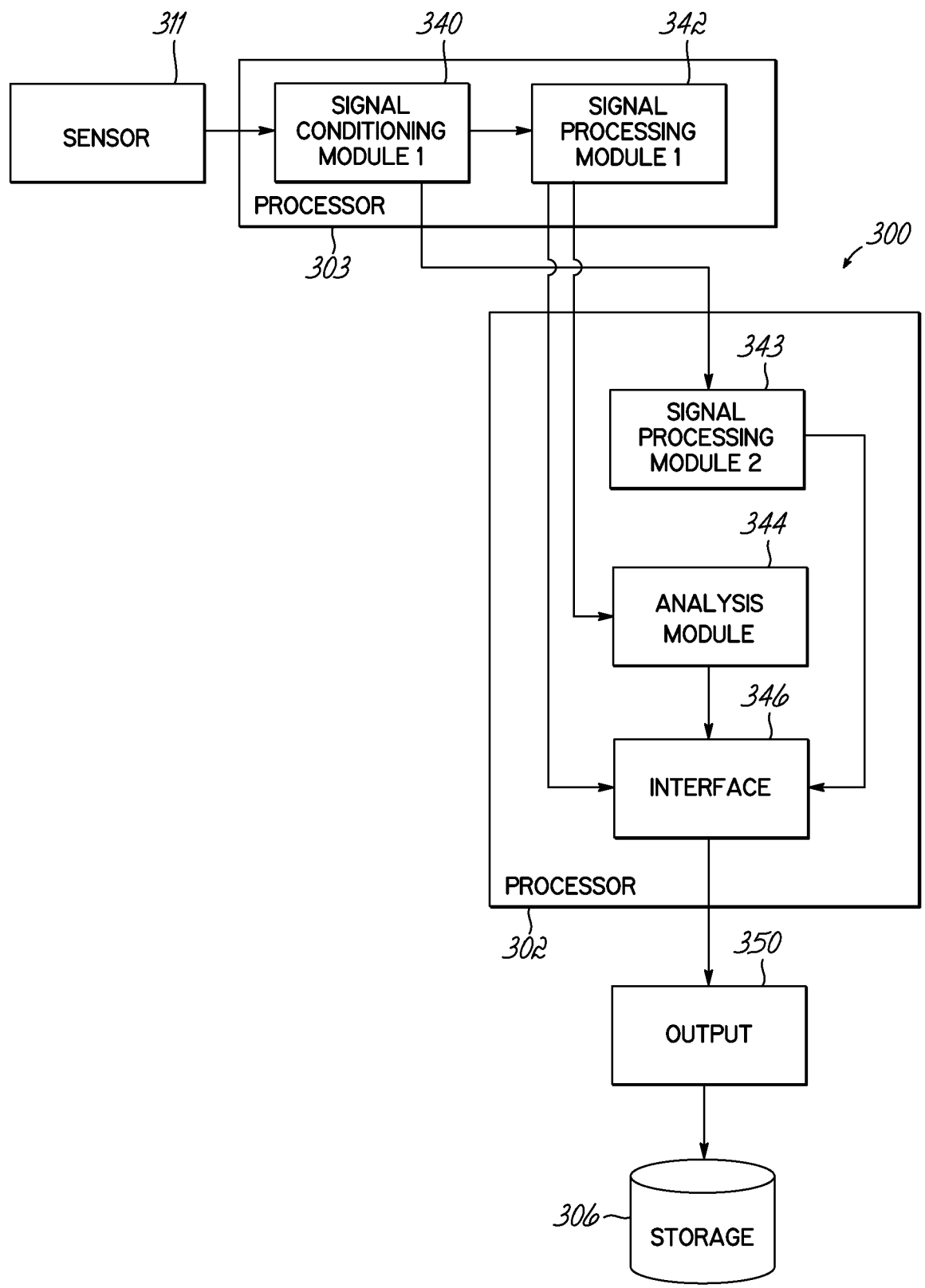

Although FIG. 25 illustrates the case of a processor 302, it can be understood that in various embodiments, the system may include one or more second processors 303, as illustrated in FIGS. 27-28. As illustrated in FIGS. 26-27, the second processor 303 may be external to the first processor 302 and optionally may be located within the first sensor 311, and may include at least one module 342 configured for post-acquisition processing of the first signal and that communicates, via a wired or wireless connection, with the first processor 302 for further processing of the signal prior to generation of an output 350.

Although FIG. 25 illustrates the case of a first sensor 311 it can be understood that the system 300 may include at least one second sensor 313 configured to record at least one second signal, as shown in FIGS. 26, 27. In various embodiments, as illustrated, the second sensor 313 communicates with the first processor 302, via a wired or wireless connection, to transmit the second signal to the first processor 302 for post-acquisition processing and analysis by modules 340, 342, 344 collocated therein. In various embodiments, the second sensor 313 may include a second processor 303 that includes at least one module 341, 343, configured to process the acquired signal.

Table 2 provides a list of examples of various primary signal captured from each that might be used for capturing a biological signal for use with the present invention. This list is exemplary only and is not intended to be inclusive.

TABLE 2

Primary Sensors and Primary Signals.

| Primary Sensor | Primary Signal Acquired |
| --- | --- |
| Photo-optic sensor (transmissive) | Blood density |
| Photo-optic sensor (reflective) | Blood density |
| Pressure transducer | Pulse pressure |
| Tonometry device | Vascular palpation |
| Strain gauge | Vessel circumference |
| Ultrasound device | Vessel diameter |
| Electrical impedance | Fluid electrical conductivity |
| Radar device | Cardiac pulses |
| Non-contact PPG (camera) | Images |

In one embodiment, the primary sensor 311 is a photo-optic sensor that acquires a photo-optic signal as described above. The photo-optic sensor may acquire the signal at a wavelength at which density changes reflect changes in density of both oxygenated and deoxygenated blood. For example, in one embodiment, the photo-optic sensor acquires the signal at wavelengths between about 700 nm and about 950 nm.

The photo-optic sensor may be either transmissive or reflective. In various embodiments, the photo-optic sensor is a reflective photo-optic sensor. The transmitter and the receiver are separated by a distance. In embodiments, the reflective photo-optic sensor is positioned on a patient's forehead or other well-vascularized skin surfaces. In other various embodiments, the photo-optic sensor is a transmissive photo-optic sensor. In embodiments, the transmissive photo-optic sensor is positioned on a patient's finger or the like and light is transmitted through the finger or the like to a receiver on the other side of the finger.

In another embodiment, the sensor is a pressure transducer that acquires a pulse pressure signal that indicates pulsatile changes in total blood volume. In embodiments, the pressure transducer is non-invasive. In other embodiments, the pressure transducer receives the pulse pressure signal from an arterial pressure line implanted in an artery.

In another embodiment, the sensor is a tonometry device that acquires a signal that measures changes in vascular tension or pressure that result from changes in blood density that occur as the pulse wave travels through the arterial bed. In embodiments, tissue is applanated to obtain the vascular pressure change.

In another embodiment, the primary sensor is a strain gauge that acquires a signal that measures changes in the circumference of an extremity that result from changes in blood density that occur as the pulse wave travels through the arterial bed.

In another embodiment, the primary sensor is an ultrasound device that acquires a signal that measures changes in the diameter of a blood vessel that result from changes in blood density that occur as the pulse wave travels through the arterial bed.

In another embodiment, the primary sensor is an electrical impedance device that acquires a signal that measures changes in electrical conductivity of the blood that result from changes in blood density that occur as the pulse wave travels through the arterial bed.

In another embodiment, the primary sensor 10 is a radar device that acquires a signal that measures changes in contraction of the cardiac muscle during a cardiac cycle.

In another embodiment, the primary sensor 10 is a camera that acquires a signal that measures changes in color, reflecting the changes in blood density that occur during each cardiac cycle.

While the present invention has been illustrated by the description of the embodiments thereof, and while the embodiments have been described in considerable detail, it is not the intention of the Applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of Applicant's general inventive concept.

What is claimed is:

1. A method of evaluating respiratory health of a patient comprising:
   receiving at least one biological signal, having respiratory and cardiac components and a waveform curve in the time domain, from a sensor in operative communication with the patient;
   using at least one processor, processing the at least one biological signal and computing a respiration waveform curve that is reflective of the respiration of the patient and indicates the respiratory component of the at least one biological signal;
   determining a correlation between the at least one biological signal and respiration waveform curve and determining a respective correlation coefficient that indicates what portion of a content in the at least one biological signal is contributed by the respiratory component;
   performing a frequency analysis on the at least one biological signal to obtain frequency spectral components associated with the respiratory and cardiac components of the at least one biological signal;
   determining a respiration metric to evaluate frequency spectral components associated with the respiratory component against all the frequency spectral components of the at least one biological signal through a ratio of fundamental and harmonic frequency spectral components associated with the respiratory component of the at least one biological signal to total fundamental and harmonic frequency spectral components for the respiratory and cardiac components of the at least one biological signal;
   additively combining the correlation coefficient and the respiration metric and forming a respiratory stress metric that reflects when the respiratory component dominates the at least one biological signal;
   determining a respiration rate;
   using the respiratory stress metric and respiration rate and determining a respiratory stress condition for the patient from a plurality of possible respiratory conditions including one or more of the following: normal, bradypnea, tachypnea, hypopnea, hyperpnea, and sleep apnea.

2. The method of claim 1 further comprising scaling the correlation coefficient and respiration metric before additively combining to form the respiratory stress metric.

3. The method of claim 1 further comprising comparing the respiratory stress metric to a threshold for determining the respiratory stress condition of the patient.

4. The method of claim 1 further comprising displaying the determined respiratory stress condition for a user.

5. The method of claim 1 further comprising forming a respiratory stress metric at an initial time for providing a baseline respiratory stress metric for the patient and later in time following the initial time providing a subsequent respiratory stress metric, determining a percent change in the subsequent respiratory stress metric from the baseline respiratory stress metric.

6. The method of claim 1 wherein the at least one biological signal is a photoplethysmogram (PPG) signal.

7. The method of claim 1 wherein the respiration waveform curve is computed with a B-spline curve fit analysis.

8. The method of claim 1 wherein the respiration rate is calculated by at least one of: using the frequency analysis on the respiration waveform curve and determining a respiration rate fundamental frequency or using the frequency analysis and the determined respiration metric.

9. The method of claim 1 further comprising resampling the respiration waveform curve and aligning the respiration waveform curve with the at least one biological signal for determining the correlation coefficient.

10. A system comprising:
    a sensor configured for operative communication with a patient to generate at least one biological signal having respiratory and cardiac components and a waveform curve in the time domain;
    a device with at least one processor, the device configured for being coupled with the sensor;
    program code configured to be executed on the at least one processor, the program code causing the processor of the device to process the at least one biological signal and compute a respiration waveform curve that is reflective of the respiration of the patient and indicates the respiratory component of the at least one biological signal, to determine a correlation between the at least one biological signal and respiration waveform curve and determine a respective correlation coefficient that indicates what portion of a content in the at least one biological signal is contributed by the respiratory component, to perform a frequency analysis on the at least one biological signal to obtain frequency spectral components associated with the respiratory and cardiac components of the at least one biological signal and determine a respiration metric to evaluate frequency spectral components associated with the respiratory component against all the frequency spectral components of the at least one biological signal through a ratio of fundamental and harmonic frequency spectral components associated with the respiratory component of the at least one biological signal to total fundamental and harmonic frequency spectral components for the respiratory and cardiac components of the at least one biological signal, and to additively combine the correlation coefficient and the respiration metric and form a respiratory stress metric that reflects when the respiratory component dominates the at least one biological signal, and to determine a respiration rate and to use the respiratory stress metric and respiration rate to determine a respiratory stress condition for the patient from a plurality of possible respiratory conditions including one or more of the following: normal, bradypnea, tachypnea, hypopnea, hyperpnea, and sleep apnea, the device configured with a display.

11. The system of claim 10 wherein the program code is configured for scaling the correlation coefficient and respiration metric before combining to form the respiratory stress metric.

12. The system of claim 10 wherein the program code is configured for comparing the respiratory stress metric to a threshold for determining the respiratory stress condition of the patient.

13. The system of claim 10 wherein the program code is configured for displaying at least one of the respiratory stress metric and the determined respiratory stress condition for a user.

14. The system of claim 13 wherein the program code is configured for calculating the respiration rate by at least one of: using the frequency analysis on the respiration waveform curve and determining a respiration rate fundamental frequency or using the frequency analysis and the determined respiration metric.

15. The system of claim 10 wherein the program code is configured for providing a baseline respiratory stress metric for the patient and providing a subsequent respiratory stress metric, and determining a percent change in the subsequent respiratory stress metric from the baseline respiratory stress metric.

16. The system of claim 10 wherein the sensor is configured for generating at least one photoplethysmogram (PPG) biological signal.

17. The system of claim 10 wherein the program code is configured for generating the respiration waveform curve with a B-spline curve fit analysis.

18. The system of claim 10 wherein the program code is configured for resampling the respiration rate waveform curve and aligning the respiration rate waveform curve with the at least one biological signal for determining the correlation coefficient.

19. A computer program product comprising:

a non-transitory computer readable storage medium; and program code stored on the non-transitory computer readable storage medium and configured to be executed by a processor to cause the processor to process a biological signal having respiratory and cardiac components and a waveform curve in the time domain from a sensor configured for operative communication with a patient and compute a respiration waveform curve that is reflective of the respiration of the patient and indicates the respiratory component of the biological signal, to determine a correlation between the biological signal and respiration waveform curve and determine a respective correlation coefficient that indicates what portion of a content in the biological signal is contributed by the respiratory component, to perform a frequency analysis on the biological signal to obtain frequency spectral components associated with the respiratory and cardiac components of the biological signal and determine a respiration metric to evaluate frequency spectral components associated with the respiratory component against all the frequency spectral components of the biological signal through a ratio of fundamental and harmonic frequency spectral components associated with the respiratory component of the biological signal to total fundamental and harmonic frequency spectral components for the biological signal, and to additively combine the correlation coefficient and the respiration metric and form a respiratory stress metric that reflects when the respiratory component dominates the biological signal, and to determine a respiration rate and to use the respiratory stress metric and respiration rate to determine a respiratory stress condition for the patient from a plurality of possible respiratory conditions including one or more of the following: normal, bradypnea, tachypnea, hypopnea, hyperpnea, and sleep apnea.

\* \* \* \* \*